US011284238B1

(12) United States Patent
Wen

(10) Patent No.: US 11,284,238 B1
(45) Date of Patent: Mar. 22, 2022

(54) EMERGENCY SIGNS EARLY DETECTION, ALERT AND RESPONSE SYSTEMS AND METHODS OF USING THE SAME

(71) Applicant: Xiao Jun Wen, Norcross, GA (US)

(72) Inventor: Xiao Jun Wen, Norcross, GA (US)

( * ) Notice: Subject to any disclaimer, the term of this patent is extended or adjusted under 35 U.S.C. 154(b) by 0 days.

(21) Appl. No.: 17/241,054

(22) Filed: Apr. 26, 2021

(51) Int. Cl.
| | |
|---|---|
| *H04W 4/90* | (2018.01) |
| *H04W 4/029* | (2018.01) |
| *G16H 80/00* | (2018.01) |
| *G16H 40/67* | (2018.01) |
| *H04L 67/12* | (2022.01) |

(52) U.S. Cl.
CPC .............. *H04W 4/90* (2018.02); *G16H 40/67* (2018.01); *G16H 80/00* (2018.01); *H04L 67/12* (2013.01); *H04W 4/029* (2018.02)

(58) Field of Classification Search
None
See application file for complete search history.

(56) References Cited

U.S. PATENT DOCUMENTS

| 10,229,575 | B2* | 3/2019 | Bauer | ...................... H04Q 9/00 |
| 2012/0108917 | A1* | 5/2012 | Libbus | .................. A61B 5/1115 |
| | | | | 600/301 |
| 2013/0082837 | A1* | 4/2013 | Cosentino | .............. A61B 5/002 |
| | | | | 340/539.12 |

* cited by examiner

*Primary Examiner* — Adolf Dsouza
(74) *Attorney, Agent, or Firm* — Ming Jiang; MM IP Services LLC

(57) ABSTRACT

The present disclosure relates to an emergency signs early detection, alert and response system (ESEDARS). The ESEDARS includes an ESEDARS server, a patient database, a communication system, and many ESEDARS personal devices for many patients, one or more ESEDARS personal device(s) for each patient. Each ESEDARS personal device has a set of patient biological information collection devices (PBICD) monitoring biological information of each patient constantly. Biological information of each patient is collected and transmitted to ESEDARS server for processing using artificial intelligence algorithms to detect early emergency signs before emergency occurs. When at least one PBICD detects certain type of biological information that exceeds a normal range of baseline biological information stored in the patient database, ESEDARS determines the patient is near or in an emergency, and coordinates immediate medical assistance to the patient based on the patient information received and retrieved from the patient database.

20 Claims, 8 Drawing Sheets

EMERGENCY SIGNS EARLY DETECTION, ALERT AND RESPONSE SYSTEMS AND METHODS OF USING THE SAME

FIELD

The present disclosure generally relates to medical devices, and more particularly to emergency signs early detection, alert and response systems (hereinafter ESEDARS), and methods of using the ESEDARSs.

BACKGROUND

According to World Health Organization (WHO), of the 56.9 million deaths worldwide in 2016, more than half (30.7 million or 54%) were due to these top three causes related to heart conditions, including ischemic heart diseases, stroke, and chronic obstructive pulmonary. Ischemic heart disease, stroke and chronic obstructive pulmonary are the world's biggest killers, accounting for a combined 18.2 million deaths in 2016. These diseases have remained the leading causes of death globally in the last 15 years.

Majority of deaths from ischemic heart disease and stroke are preventable if the patients receive care and take the appropriate medications immediately; or if the early symptoms of heart attacks and/or stroke are detected and recognized, and preventive treatments are given before stroke or heart attack. The most important things for a patient to survive from medical emergencies include three key components, early signs recognition or detection to prevent emergency from happening; patients, medical professionals, emergency responders, and care takers are immediately alerted or noticed; and patients, medical professionals, emergency responders, and care takers work together to respond promptly to provide the appropriate care needed to survive or avoid serious complications.

Thus, it is desirable to have an ESEDARS to ensure: the early signs or precursors of a medical emergency can be detected as early as possible to prevent it from happening, the patient receives immediate medical care by trained professionals, the patient receives and takes appropriate medications, and nearby emergency dispatch centers are notified and ambulance and medical emergency staff arrive at the scene in shortest possible time.

Therefore, a heretofore unaddressed needs still exist in the art to address the aforementioned deficiencies and inadequacies.

SUMMARY

In one aspect, the present disclosure relates to an ESEDARS. In certain embodiments, the ESEDARS includes: an ESEDARS server, a patient database, a communication system, and a group of ESEDARS personal devices. In certain embodiments, each of a group of patients carries an ESEDARS personal device. Each patient registers himself/herself as well as his/her ESEDARS personal device at the ESEDARS server, collects his/her baseline biological information, and stores the baseline biological information collected in the patient database. The ESEDARS server provides immediate emergency assistance to a patient when the ESEDARS personal device of the patient detects one or more emergency signs from the patient.

In certain embodiments, the patient database is connected to and accessible by the ESEDARS server. The patient database stores patient information of the group of patients. The patient information includes personal information, medical history, a set of baseline biological information, patient contact information, and contact information of relatives, friends and other responders and local medical facilities to be notified. In certain embodiments, the communication system is connected to the ESEDARS server, and the communication system provides voice, text, and video communication over a communication network among the patient, one or more live emergency responders from a nearby emergency dispatch center, one or more patient's relatives, friends and other responders on record, and one or more nearby medical facilities to provide immediate emergency assistance to the patient when one or more emergency signs from the patient are detected.

In certain embodiments, each patient carries an ESEDARS personal device. Each ESEDARS personal device includes a set of patient biological information collection devices (hereinafter PBICD). The set of PBICDs constantly monitors the biological information of the patient and transmits the patient biological information collected to the ESEDARS server through the ESEDARS personal device, and when at least one of a set of PBICDs detects certain type of biological information that exceeds a normal range of the set of baseline biological information stored in the patient database, the ESEDARS server initiates at least voice communication between the ESEDARS server and the ESEDARS personal device of the patient through the communication system directly. Each ESEDARS personal device includes an emergency medicine storage for storing one or more patient specific emergency medicines to be used when emergency occurs.

In certain embodiments, an ESEDARS personal device indicator of the ESEDARS personal device is lit in green light when the ESEDARS personal device is in normal operation state. When an emergency signs is detected from the patient, the ESEDARS personal device indicator turns red indicating the patient is in an emergency. The ESEDARS personal device initiates an emergency call to the nearby emergency dispatch center to notify a live emergency responder with the patient's GPS location information and patient information including contact information of patient's relatives, friends and other responders on record. The live emergency responder connects to one or more patient's relatives, friends and other responders on record and a nearby medical facility to coordinate immediate medical assistance to the patient based on the patient information received and retrieved from the patient database. The live emergency responder and the ESEDARS server provide patient specific medical assistance instructions for the patient to follow including instructing the patient to take one or more patient specific emergency medicines stored in the emergency medicine storage of the ESEDARS personal device. The patient continues to communicate with the live emergency responder and the one or more patient's relatives, friends and other responders on record until an ambulance from a nearby medical facility arrives.

In certain embodiments, the communication network includes a wireless personal area network (WPAN), a wireless local area network (WLAN), a wireless metropolitan area network (WMAN), a wireless wide area network (WWAN), a cellular network, and a mobile communication network. The wireless personal area network includes: a Wi-Fi network, a Bluetooth network, an infrared network, and a Zigbee network.

In certain embodiments, the ESEDARS server includes: a server processor, a network interface controller, and a non-volatile memory. The server processor controls operations of the ESEDARS. The network interface controller connects to the communication network through a firewall connector over a firewall. The non-volatile memory stores a server operating system, a network communication module, and an emergency signs early detection, alert and response (ESE-DAR) controller. The ESEDAR controller includes a patient information storage module for accessing the patient database through a database interface, a communication control module for facilitating communication to the communication system through a communication control interface, a patient emergency signs processing module, and computer executable instructions. When executed by the server processor, the computer executable instructions perform one or more of following operations:

receiving, through patient biological information transmission channels from an ESEDARS personal device of the patient, patient biological information constantly monitored and collected by the set of PBICDs of the ESEDARS personal device;

processing, by the patient emergency signs processing module, patient biological information received, based on base line patient biological information from the patient database;

initiating, by the ESEDARS server, an emergency voice call to the ESEDARS personal device of the patient through the communication system, when at least one of the set of PBICDs detects certain type of biological information that exceeds a normal range of the set of baseline biological information stored in the patient database;

initiating, by the ESEDARS server, an emergency call to the nearby emergency dispatch center to notify the live emergency responder with the patient's GPS location information and patient information including contact information of patient's relatives, friends and other responders on record;

connecting, through the communication control module, the ESEDARS personal device carried by the patient to the patient's relatives, friends and other responders on record and a nearby medical facility to coordinate immediate medical assistance to the patient; and transmitting, through the communication control module, a set of patient specific medical assistance instructions through the communication control interface and the live emergency responder for the patient to follow including instructing the patient to take one or more patient specific emergency medicines stored in the emergency medicine storage of the ESEDARS personal device, and the patient continues to communicate with the live emergency responder and the one or more patient's relatives, friends and other responders on record until an ambulance from the nearby medical facility arrives.

In certain embodiments, the ESEDARS personal device collects patient biological information from the set of PBICDs connected through the patient biological information transmission channels. The set of PBICDs includes: a microphone and a speaker for allowing the patient to make and receive voice calls, to generate voice samples of the patient, and to provide voice instructions to the patient; one or more video cameras for monitoring the patient through videos and still images; one or more electroencephalograms, for monitoring electroencephalography of the patient; one or more electrocardiograms, for monitoring electrocardiography of the patient; a breath analyzer, for analyzing breath samples of the patient; a blood glucose meter, for monitoring blood sugar of the patient; an oximeter, for monitoring blood oxygen concentration of the patient; a blood pressure meter, for monitoring pulse rate and blood pressure of the patient; a stethoscope, for monitoring breathing, heart, thoracic, arterial, intravenous, uterine, fetal, intestinal and other sounds of the patient; and a thermometer, for monitoring the body temperature of the patient.

In certain embodiments, the ESEDARS personal device further includes a display screen to receive and display text messages and carry out video calls.

In certain embodiments, the communication among the patient, the live emergency responder, the patient's relatives, friends and other responders on record and the nearby medical facility includes: a mobile voice call; a mobile videotelephony call; a landline voice call; a videotelephony call over the Internet; a text message over a mobile phone; a text message over a group of social media platforms; and a videotelephony call over the group of social media platforms.

In certain embodiments, the communication system includes: a voice input module having a mobile voice input interface to receive mobile voice calls, and a landline voice input interface to receive landline voice calls; a text input module having a social media text input interface to receive text messages through the group of social media platforms, and a text message input interface to receive text messages through mobile phones; a video input module having a mobile video input interface to receive video calls over the mobile phones, and a social media video input interface to receive video calls through the group of social media platforms; a voice output module having a mobile voice output interface to make mobile voice calls, and a landline voice output interface to make landline voice calls; a text output module having a social media text output interface to transmit text messages through the group of social media platforms, and a text message output interface to transmit text messages through the mobile phones; a video output module having a mobile video output interface to make video calls over the mobile phones, and a social media video output interface to make video calls through the group of social media platforms; a speech to text conversion module for converting voice input to text input; a live emergency responder interface module for the live emergency responder to receive and make conference calls among the patient, the live emergency responder, the patient's relatives, friends and other responders on record and the nearby medical facility through voice calls, text messages, and video calls; and a text to speech conversion module to make voice calls to the patient through the ESEDARS personal device.

In certain embodiments, the communication control interface includes: a voice input terminal connected to the voice input module; a text input terminal connected to the text input module; a video input terminal connected to the video input module; a voice output terminal connected to the voice output module; a text output terminal connected to the text output module; and a video output terminal connected to the video output module.

In certain embodiments, the ESEDARS personal device includes: a processor, a network interface controller, the emergency medicine storage, and a non-volatile memory. The processor controls operations of the ESEDARS personal device. The network interface controller facilitates the communication among the ESEDARS personal device, the ESEDARS server and the communication system. The emergency medicine storage includes one or more emergency medicine compartments, where one or more patient specific emergency medicines for the patient are stored. The non-volatile memory stores an operating system, a GPS module for detecting the GPS location of the patient carrying the ESEDARS personal device, and a patient emergency signs early detection, alert and response (ESEDAR) controller. The patient ESEDAR controller includes a patient information storage module for storing the patient's information, a patient communication control module for facilitating communication through the network interface controller to the ESEDARS server and the communication system over the communication network, a patient emergency signs processing module and computer executable instructions. When executed by the processor, the computer executable instructions perform one or more of following operations:

receiving, through the patient biological information transmission channels from an ESEDARS personal device, patient biological information constantly monitored and collected by the set of PBICDs of the ESEDARS personal device;

transmitting, through the patient communication control module, patient biological information received to the ESEDARS server for processing by the patient emergency signs processing module;

receiving, from the ESEDARS server, at least voice communication through the communication system directly, when at least one of the set of PBICDs detects certain type of biological information that exceeds a normal range of the set of baseline biological information stored in the patient database;

initiating, by the ESEDARS personal device, an emergency call to the nearby emergency dispatch center to notify the live emergency responder with the patient's GPS location information and patient information including contact information of patient's relatives, friends and other responders on record;

connecting, the ESEDARS personal device to the patient's relatives, friends and other responders on record and a nearby medical facility through the patient communication control module to coordinate immediate medical assistance to the patient based on the patient information from the patient information storage module;

receiving, through the ESEDARS personal device, the set of patient specific medical assistance instructions from the live emergency responder for the patient to follow including instructing the patient to take one or more patient specific emergency medicines stored in the emergency medicine storage of the ESEDARS personal device; and maintaining, communication between the patient and the live emergency responder and the one or more patient's relatives, friends and other responders on record until an ambulance from the nearby medical facility arrives.

In one embodiment, the ESEDARS personal device is a robot. The robot follows the patient around home and office, monitors the patient's biological information through the PBICDs, and when the robot notices certain irregularities, the robot offers more tests and examinations, and provides immediate assistance. In another embodiment, the ESEDARS personal device is a portable ESEDARS personal device. The portable ESEDARS personal device is carried with the patient and the portable ESEDARS personal device also stores one or more patient specific emergency medicines. In yet another embodiment, the portable ESEDARS personal device is a stationary ESEDARS personal device. The stationary ESEDARS personal device is placed at home or work place of the patient and the stationary ESEDARS personal device also stores one or more patient specific emergency medicines. In yet another embodiment, the ESEDARS personal device can be a group of public stationary ESEDARS personal devices. These public stationary ESEDARS personal devices are placed in public places and each of the public stationary ESEDARS personal devices stores at least one of several common emergency medicines.

In another aspect, the present disclosure relates to a method of using an ESEDARS. In certain embodiments, the method includes:

registering, by a group of patients, each of the group of patients, and a group of ESEDARS personal devices, one corresponding ESEDARS personal device for each patient, at an ESEDARS server of the ESEDARS, collecting, a set of baseline biological information for each patient, and storing the baseline biological information collected in the patient database, patient information of each of the patients is stored in a patient database of the ESEDARS, and the ESEDARS provide immediate emergency assistance to each of the patients when an ESEDARS personal device detects one or more emergency signs from a corresponding patient;

constantly monitoring and collecting, by a set of PBICDs of the group of ESEDARS personal devices, patient biological information of each of the patients;

receiving, through a patient communication control module from an ESEDARS personal device, the patient biological information constantly monitored and collected by the set of PBICDs of the ESEDARS personal device;

processing, through a patient emergency signs processing module of the ESEDARS server of the ESEDARS, the patient biological information received, and comparing the patient biological information received with the set of baseline biological information stored in the patient database;

initiating, by the ESEDARS server, at least voice communication between the ESEDARS server and the ESEDARS personal device of the patient through the communication system directly, when at least one of a set of PBICDs detects certain type of biological information that exceeds a normal range of the set of baseline biological information stored in the patient database;

initiating, by the ESEDARS server, an emergency call to a nearby emergency dispatch center to notify a live emergency responder with the patient's GPS location information and patient information including contact information of patient's relatives, friends and other responders on record;

connecting, by the live emergency responder, to one or more patient's relatives, friends and other responders on record and a nearby medical facility to coordinate immediate medical assistance to the patient based on the patient information received and retrieved from the patient database;

providing, by the live emergency responder and the ESEDARS server, patient specific medical assistance instructions for the patient to follow including instructing the patient to take one or more patient specific emergency medicines stored in an emergency medicine storage of the ESEDARS personal device; and communicating, by the patient through a communication system of the ESEDARS, with the live emergency responder and the one or more patient's relatives, friends and other responders on record until an ambulance from a nearby medical facility arrives.

In certain embodiments, the ESEDARS includes: the ESEDARS server, the patient database, the communication system, and the group of ESEDARS personal devices. In certain embodiments, each of the group of patients carries an ESEDARS personal device. Each patient registers himself/herself as well as his/her ESEDARS personal device at the ESEDARS server, collects his/her baseline biological information, and stores the baseline biological information collected in the patient database. The ESEDARS server provides immediate emergency assistance to a patient when an ESEDARS personal device of the patient detects one or more emergency signs from the patient.

In certain embodiments, the patient database is connected to and accessible by the ESEDARS server. The patient database stores patient information of the group of patients. The patient information includes personal information, medical history, a set of baseline biological information, patient contact information, and contact information of relatives, friends and other responders and local medical facilities to be notified. In certain embodiments, the communication system is connected to the ESEDARS server, and the communication system provides voice, text, and video communication over a communication network among the patient, one or more live emergency responders from the nearby emergency dispatch center, one or more patient's relatives, friends and other responders on record, and one or more nearby medical facilities to provide immediate emergency assistance to the patient when one or more emergency signs from the patient are detected.

In certain embodiments, each patient carries an ESEDARS personal device. Each ESEDARS personal device includes the set of PBICDs. The set of PBICDs constantly monitors the biological information of the patient and transmits the patient biological information collected to the ESEDARS server through the ESEDARS personal device. When at least one of the set of PBICDs detects certain type of biological information that exceeds a normal range of the set of baseline biological information stored in the patient database, the ESEDARS server initiate at least voice communication between the ESEDARS server and the ESEDARS personal device of the patient through the communication system directly. Each ESEDARS personal device includes the emergency medicine storage for storing one or more patient specific emergency medicines to be used when emergency occurs.

In certain embodiments, the communication network includes a wireless personal area network (WPAN), a wireless local area network (WLAN), a wireless metropolitan area network (WMAN), a wireless wide area network (WWAN), a cellular network, and a mobile communication network. The wireless personal area network includes: a Wi-Fi network, a Bluetooth network, an infrared network, and a Zigbee network.

In certain embodiments, the ESEDARS server includes: a server processor, a network interface controller, and a non-volatile memory. The server processor controls operations of the ESEDARS. The network interface controller connects to the communication network through a firewall connector over a firewall. The non-volatile memory stores a server operating system, a network communication module, and an ESEDAR controller. The ESEDAR controller includes a patient information storage module for accessing the patient database through a database interface, a communication control module for facilitating communication to the communication system through a communication control interface, the patient emergency signs processing module, and computer executable instructions. When executed by the server processor, the computer executable instructions perform one or more of following operations:

receiving, through the patient communication control module from the group of ESEDARS personal devices, patient biological information constantly monitored and collected by the set of PBICDs of the group of ESEDARS personal devices;

processing, through the patient emergency signs processing module, the patient biological information received, and comparing the patient biological information received with the set of baseline biological information stored in the patient database;

initiating, by the ESEDARS server, at least voice communication between the ESEDARS server and the ESEDARS personal device of the patient through the communication system directly, when at least one of the set of PBICDs detects certain type of biological information that exceeds a normal range of the set of baseline biological information stored in the patient database;

initiating, by the ESEDARS server, an emergency call to the nearby emergency dispatch center to notify the live emergency responder with the patient's GPS location information and patient information including contact information of patient's relatives, friends and other responders on record;

connecting, the ESEDARS personal device to the patient's relatives, friends and other responders on record and a nearby medical facility through the patient communication control module to coordinate immediate medical assistance to the patient based on the patient information from the patient information storage module;

transmitting, through the communication control module, a set of patient specific medical assistance instructions through the communication control interface and the live emergency responder for the patient to follow including instructing the patient to take one or more patient specific emergency medicines stored in the emergency medicine storage of the ESEDARS personal device, and maintaining, by the patient, communication with the live emergency responder and the one or more patient's relatives, friends and other responders on record until an ambulance from the nearby medical facility arrives.

In certain embodiments, the ESEDARS personal device collects patient biological information from the set of PBICDs connected through patient biological information transmission channels. The set of PBICDs includes: a microphone and a speaker for allowing the patient to make and receive voice calls, to generate voice samples of the patient, and to provide voice instructions to the patient; one or more video cameras for monitoring the patient through videos and still images; one or more electroencephalograms, for monitoring electroencephalography of the patient; one or more electrocardiograms, for monitoring electrocardiography of the patient; a breath analyzer, for analyzing breath samples of the patient; a blood glucose meter, for monitoring blood sugar of the patient; an oximeter, for monitoring blood oxygen concentration of the patient; a blood pressure meter, for monitoring pulse rate and blood pressure of the patient; a stethoscope, for monitoring breathing, heart, thoracic, arterial, intravenous, uterine, fetal, intestinal and other sounds of the patient; and a thermometer, for monitoring the body temperature of the patient.

In certain embodiments, the ESEDARS personal device further includes a display screen to receive and display text messages and carry out video calls.

In certain embodiments, the communication system includes: a voice input module having a mobile voice input interface to receive mobile voice calls, and a landline voice input interface to receive landline voice calls; a text input module having a social media text input interface to receive text messages through the group of social media platforms, and a text message input interface to receive text messages through mobile phones; a video input module having a mobile video input interface to receive video calls over the mobile phones, and a social media video input interface to receive video calls through the group of social media platforms; a voice output module having a mobile voice output interface to make mobile voice calls, and a landline voice output interface to make landline voice calls; a text output module having a social media text output interface to transmit text messages through the group of social media platforms, and a text message output interface to transmit text messages through the mobile phones; a video output module having a mobile video output interface to make video calls over the mobile phones, and a social media video output interface to make video calls through the group of social media platforms; a speech to text conversion module for converting voice input to text input; a live emergency responder interface module for the live emergency responder to receive and make conference calls among the patient, the live emergency responder, the patient's relatives, friends and other responders on record and the nearby medical facility through voice calls, text messages, and video calls; and a text to speech conversion module to make voice calls to the patient through the ESEDARS personal device.

In certain embodiments, the communication among the patient, the live emergency responder, the patient's relatives, friends and other responders on record and the nearby medical facility includes: a mobile voice call; a mobile videotelephony call; a landline voice call; a videotelephony call over the Internet; a text message over a mobile phone; a text message over a group of social media platforms; and a videotelephony call over the group of social media platforms. The communication control interface includes: a voice input terminal connected to the voice input module; a text input terminal connected to the text input module; a video input terminal connected to the video input module; a voice output terminal connected to the voice output module; a text output terminal connected to the text output module; and a video output terminal connected to the video output module.

the ESEDARS personal device includes: a processor, a network interface controller, the emergency medicine storage, and a non-volatile memory. The processor controls operations of the ESEDARS personal device. The network interface controller facilitates the communication among the ESEDARS personal device, the ESEDARS server and the communication system. The emergency medicine storage includes one or more emergency medicine compartments, where one or more patient specific emergency medicines for the patient are stored. The non-volatile memory stores an operating system, a GPS module for detecting the GPS location of the patient carrying the ESEDARS personal device, and a patient emergency signs early detection, alert and response (ESEDAR) controller. The patient ESEDAR controller includes a patient information storage module for storing the patient's information, the patient communication control module for facilitating communication through the network interface controller to the ESEDARS server and the communication system over the communication network, a patient emergency signs processing module and computer executable instructions. When executed by the processor, the computer executable instructions perform one or more of following operations:

receiving, through the patient biological information transmission channels from an ESEDARS personal device, patient biological information constantly monitored and collected by the set of PBICDs of the ESEDARS personal device;

transmitting, through the patient communication control module, patient biological information received to the ESEDARS server for processing by the patient emergency signs processing module;

receiving, from the ESEDARS server, at least voice communication through the communication system directly, when at least one of the set of PBICDs detects certain type of biological information that exceeds a normal range of the set of baseline biological information stored in the patient database;

initiating, by the ESEDARS personal device, an emergency call to the nearby emergency dispatch center to notify the live emergency responder with the patient's GPS location information and patient information including contact information of patient's relatives, friends and other responders on record;

connecting, the ESEDARS personal device to the patient's relatives, friends and other responders on record and a nearby medical facility through the patient communication control module to coordinate immediate medical assistance to the patient based on the patient information from the patient information storage module;

receiving, through the ESEDARS personal device, the set of patient specific medical assistance instructions from the live emergency responder for the patient to follow including instructing the patient to take one or more patient specific emergency medicines stored in the emergency medicine storage of the ESEDARS personal device; and maintaining, communication between the patient and the live emergency responder and the one or more patient's relatives, friends and other responders on record until an ambulance from the nearby medical facility arrives.

In one embodiment, the ESEDARS personal device is a robot. The robot follows the patient around home and office, monitors the patient's biological information through the PBICDs, and when the robot notices certain irregularities, the robot offers more tests and examinations, and provides immediate assistance. In another embodiment, the ESEDARS personal device is a portable ESEDARS personal device. The portable ESEDARS personal device is carried with the patient and the portable ESEDARS personal device also stores one or more patient specific emergency medicines. In yet another embodiment, the portable ESEDARS personal device is a stationary ESEDARS personal device. The stationary ESEDARS personal device is placed at home or work place of the patient and the stationary ESEDARS personal device also stores one or more patient specific emergency medicines. In yet another embodiment, the ESEDARS personal device can be a group of public stationary ESEDARS personal devices. These public stationary ESEDARS personal devices are placed in public places and each of the public stationary ESEDARS personal devices stores at least one of several common emergency medicines.

These and other aspects of the present disclosure will become apparent from the following description of the preferred embodiment taken in conjunction with the following drawings, although variations and modifications therein may be affected without departing from the spirit and scope of the novel concepts of the disclosure.

BRIEF DESCRIPTION OF THE DRAWINGS

The accompanying drawings illustrate one or more embodiments of the present disclosure, and features and benefits thereof, and together with the written description, serve to explain the principles of the present invention. Wherever possible, the same reference numbers are used throughout the drawings to refer to the same or like elements of an embodiment, and wherein.

DETAILED DESCRIPTION

Figure 1:
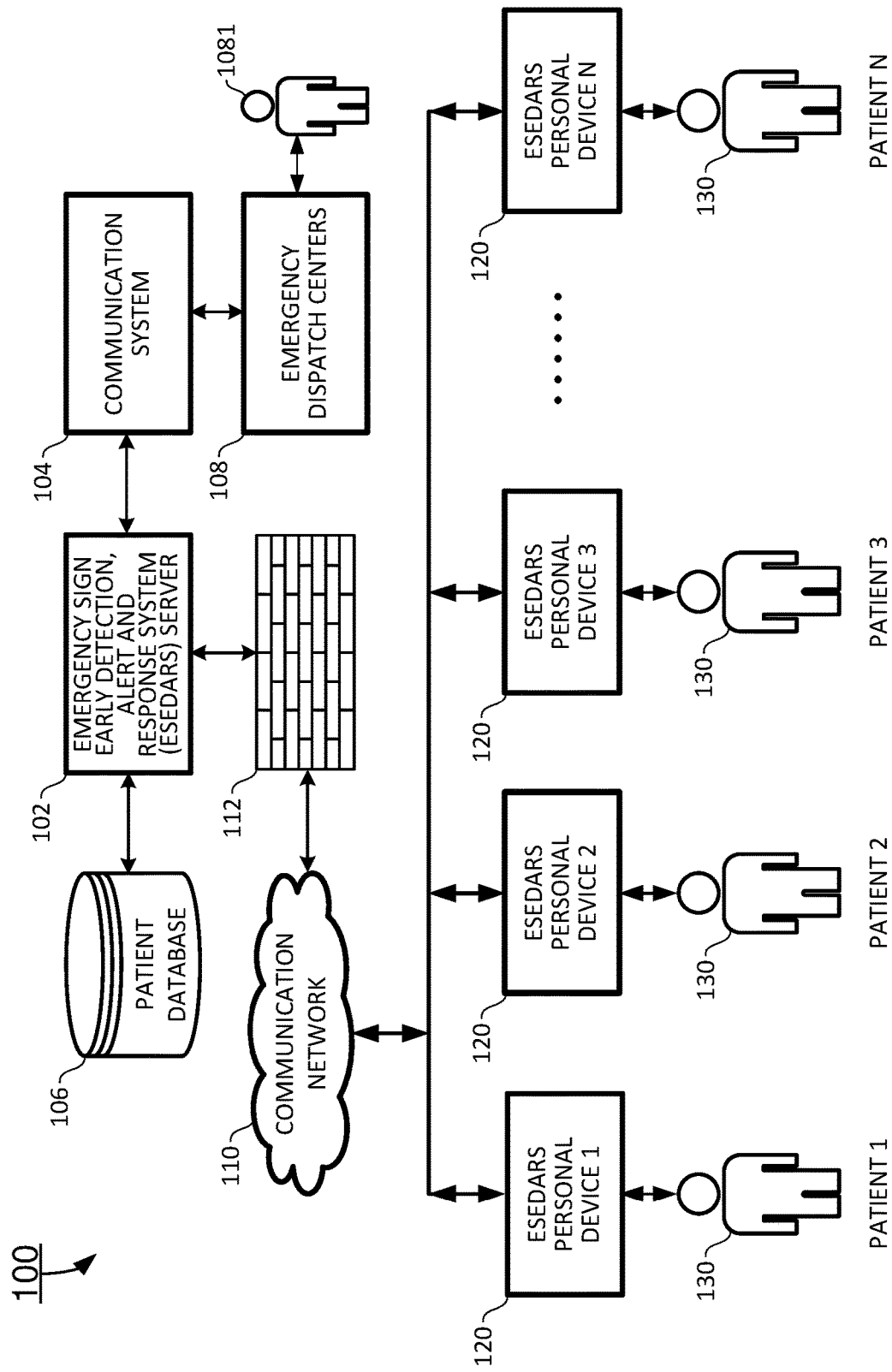
FIG. 1 shows a block diagram of an ESEDARS according to certain embodiments of the present disclosure.

The present disclosure is more particularly described in the following examples that are intended as illustrative only since numerous modifications and variations therein will be apparent to those skilled in the art. Various embodiments of the disclosure are now described in detail. Referring to the drawings, like numbers, if any, indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present disclosure. Additionally, some terms used in this specification are more specifically defined below.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the disclosure or of any exemplified term. Likewise, the disclosure is not limited to various embodiments given in this specification.

Unless otherwise defined, all technical and scientific terms used herein have the same meaning as commonly understood by one of ordinary skill in the art to which this disclosure pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "plurality" means two or more.

As used herein, the terms "comprising," "including," "carrying," "having," "containing," "involving," and the like are to be understood to be open-ended, i.e., to mean including but not limited to.

As used herein, the phrase at least one of A, B, and C should be construed to mean a logical (A or B or C), using a non-exclusive logical OR. It should be understood that one or more steps within a method may be executed in different order (or concurrently) without altering the principles of the present disclosure.

As used herein, the term module may refer to, be part of, or include an Application Specific Integrated Circuit (ASIC); an electronic circuit; a combinational logic circuit; a field programmable gate array (FPGA); a processor (shared, dedicated, or group) that executes code; other suitable hardware components that provide the described functionality; or a combination of some or all of the above, such as in a system-on-chip. The term module may include memory (shared, dedicated, or group) that stores code executed by the processor.

The term code, as used above, may include software, firmware, and/or microcode, and may refer to programs, routines, functions, classes, and/or objects. The term shared, as used above, means that some or all code from multiple modules may be executed using a single (shared) processor. In addition, some or all code from multiple modules may be stored by a single (shared) memory. The term group, as used above, means that some or all code from a single module may be executed using a group of processors. In addition, some or all code from a single module may be stored using a group of memories.

The apparatuses and methods described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

The present disclosure will now be described more fully hereinafter with reference to the accompanying drawings FIGS. 1 through 8, in which embodiments of the disclosure are shown. This disclosure may, however, be embodied in many different forms and should not be construed as limited to the embodiments set forth herein; rather, these embodiments are provided so that this disclosure will be thorough and complete, and will fully convey the scope of the disclosure to those skilled in the art. Like numbers refer to like elements throughout.

In one aspect, the present disclosure relates to an ESEDARS 100 as shown in FIG. 1. In certain embodiments, the ESEDARS 100 includes: an ESEDARS server 102, a patient database 106, a communication system 104, and a group of ESEDARS personal devices 120. In certain embodiments, each of a group of patients 130 carries an ESEDARS personal device 120. Each patient 130 registers himself/herself as well as his/her ESEDARS personal device 120 at the ESEDARS server 102, collects his/her baseline biological information, and stores the baseline biological information collected in the patient database 106.

The ESEDARS server 102 provides immediate emergency assistance to a patient 130 when the ESEDARS personal device 120 of the patient 130 detects one or more emergency signs from the patient 130.

In certain embodiments, the patient database 106 is connected to and accessible by the ESEDARS server 102. The patient database 106 stores patient information of the group of patients 130. The patient information includes personal information, medical history, a set of baseline biological information, patient contact information, and contact information of relatives, friends and other responders and local medical facilities to be notified of each registered patient 130.

In certain embodiments, the communication system 104 is connected to the ESEDARS server 102, and the communication system 104 provides voice, text, and video communication over a communication network 110 among the patients 130, one or more live emergency responders 1081 from a nearby emergency dispatch center 108, one or more patient's relatives, friends and other responders on record, and one or more nearby medical facilities to provide immediate emergency assistance to the patient 130 when one or more emergency signs from the patient 130 are detected.

Figure 5:
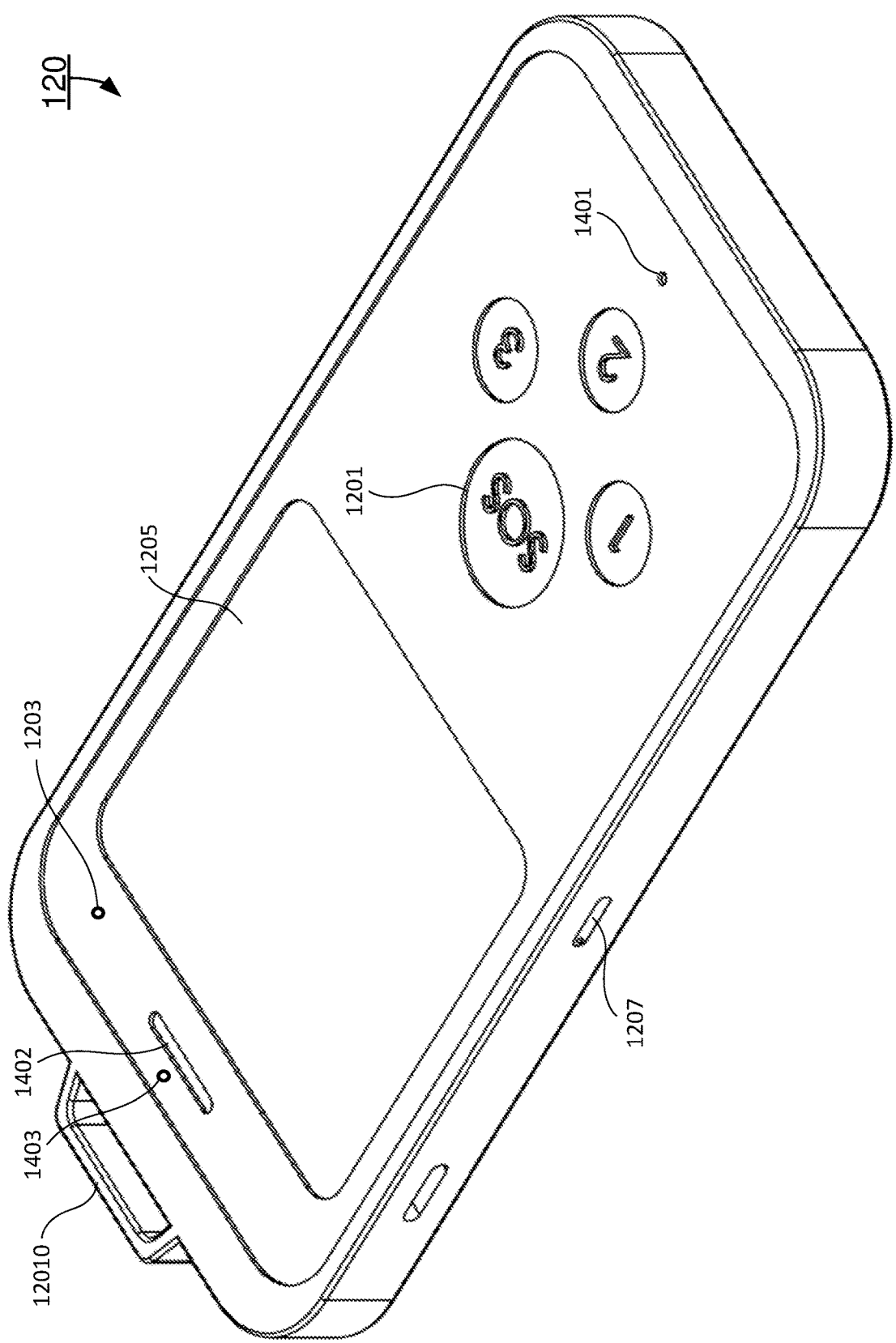
FIG. 5 shows an exemplary ESEDARS personal device according to certain embodiments of the present disclosure.

In certain embodiments, each patient 130 carries a dedicated ESEDARS personal device 120 as shown in FIG. 5. Each ESEDARS personal device 120 includes a set of PBICDs 140. The set of PBICDs 140 constantly monitors the biological information of the patient 130 and transmits the patient biological information collected to the ESEDARS server 102 through the ESEDARS personal device 120. When at least one of the set of PBICDs 140 detects certain type of biological information that exceeds a normal range of the set of baseline biological information stored in the patient database 106, the ESEDARS server 102 initiate at least voice communication between the ESEDARS server 102 and the ESEDARS personal device 120 of the patient 130 through the communication system 104 directly.

Figure 4:
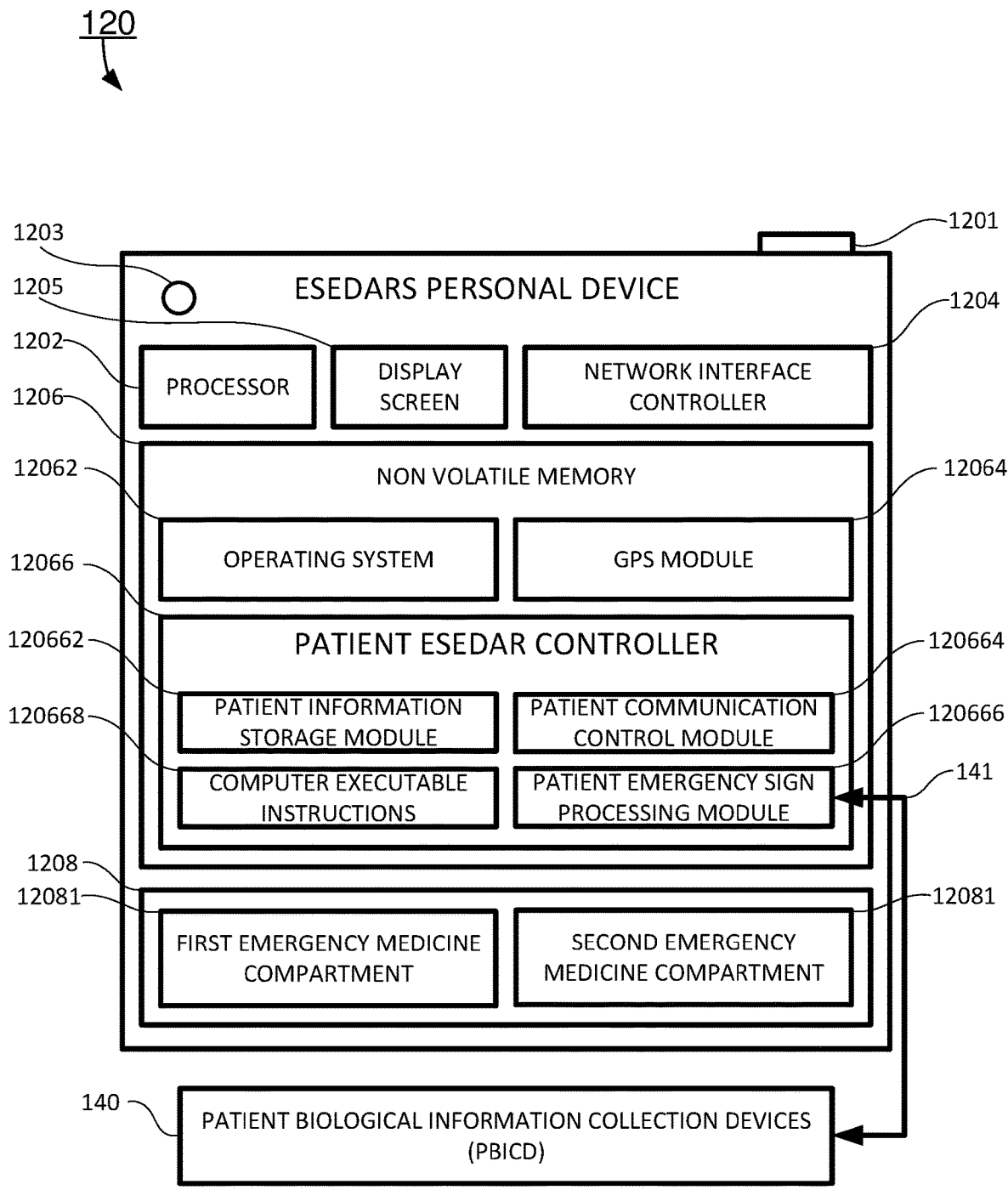
FIG. 4 illustrates a block diagram of an ESEDARS personal device according to certain embodiments of the present disclosure.

In certain embodiments, each ESEDARS personal device 120 includes an emergency medicine storage 1208. In one embodiment, the emergency medicine storage 1208 includes a first emergency medicine storage 12081, and a second emergency medicine storage 12082, as shown in FIG. 4. The first emergency medicine storage 12081 and the second emergency medicine storage 12082 store one or more patient specific emergency medicines to be used by the patient 130 carrying the ESEDARS personal device 120 when emergency occurs. In one embodiment, the patient specific emergency medicines include tissue plasminogen activator (tPA) for stroke/heart attack patients. In another embodiment, the patient specific emergency medicines include epinephrine for server allergic reaction patients. Various sizes of emergency medicine storage 1208 of ESEDARS personal devices 120 may be available to accommodate various size emergency medicines for various high risk patients 130 with various known diseases.

In certain embodiments, as shown in FIG. 5, an ESEDARS personal device indicator 1203 of the ESEDARS personal device 120 is lit in green light when the ESEDARS personal device 120 is in normal operation state. In certain embodiments, the ESEDARS personal device 120 includes an emergency button 1201. When an emergency sign is detected by the patient 130, the patient 130 presses the emergency button 1201 and the ESEDARS personal device indicator 1203 turns red indicating the patient 130 is in an emergency. Meanwhile, speaker 1402 starts beeping indicating emergency. When an emergency sign is detected from the patient 130, the ESEDARS personal device indicator 1203 turns red indicating the patient 130 is in an emergency. The ESEDARS personal device 120 initiates an emergency call to the nearby emergency dispatch center 108 to notify a live emergency responder 1081 with the patient's GPS location information and patient information including contact information of patient's relatives, friends, and other responders on record. Meanwhile, depending on the needs, ESEDARS server 102 notifies different tier responders with text or voice messages with patient's GPS location and other critical information so they can come to help. ESEDARS server 102 can also track the responses from different tiers of responders and their GIS locations so more coordinated responses can be realized. This process only ends until a responder notifies and confirms the ESEDARS server 102 of the completion of the response.

On the other hand, when an emergency sign is detected by the ESEDARS personal device 120, the ESEDARS personal device 120 initiates an emergency call to the nearby emergency dispatch center 108 to notify a live emergency responder 1081 with the patient's GPS location information and patient information including contact information of patient's relatives, friends and other responders on record. The live emergency responder 1081 connects to one or more patient's relatives, friends and other responders on record and a nearby medical facility to coordinate immediate medical assistance to the patient 130 based on the patient information received and retrieved from the patient database 106. The live emergency responder 1081 and the ESEDARS server 102 provide patient specific medical assistance instructions for the patient 130 to follow including instructing the patient 130 to take one or more patient specific emergency medicines stored in the emergency medicine storage 1208 of the ESEDARS personal device 120. The patient 130 continues to communicate with the live emergency responder 1081 and the one or more patient's relatives, friends and other responders on record until an ambulance from a nearby medical facility arrives.

In certain embodiments, the communication network 110 includes a wireless personal area network (WPAN), a wireless local area network (WLAN), a wireless metropolitan area network (WMAN), a wireless wide area network (WWAN), a cellular network, and a mobile communication network. The wireless personal area network includes: a Wi-Fi network, a Bluetooth network, an infrared network, and a Zigbee network.

Figure 2:
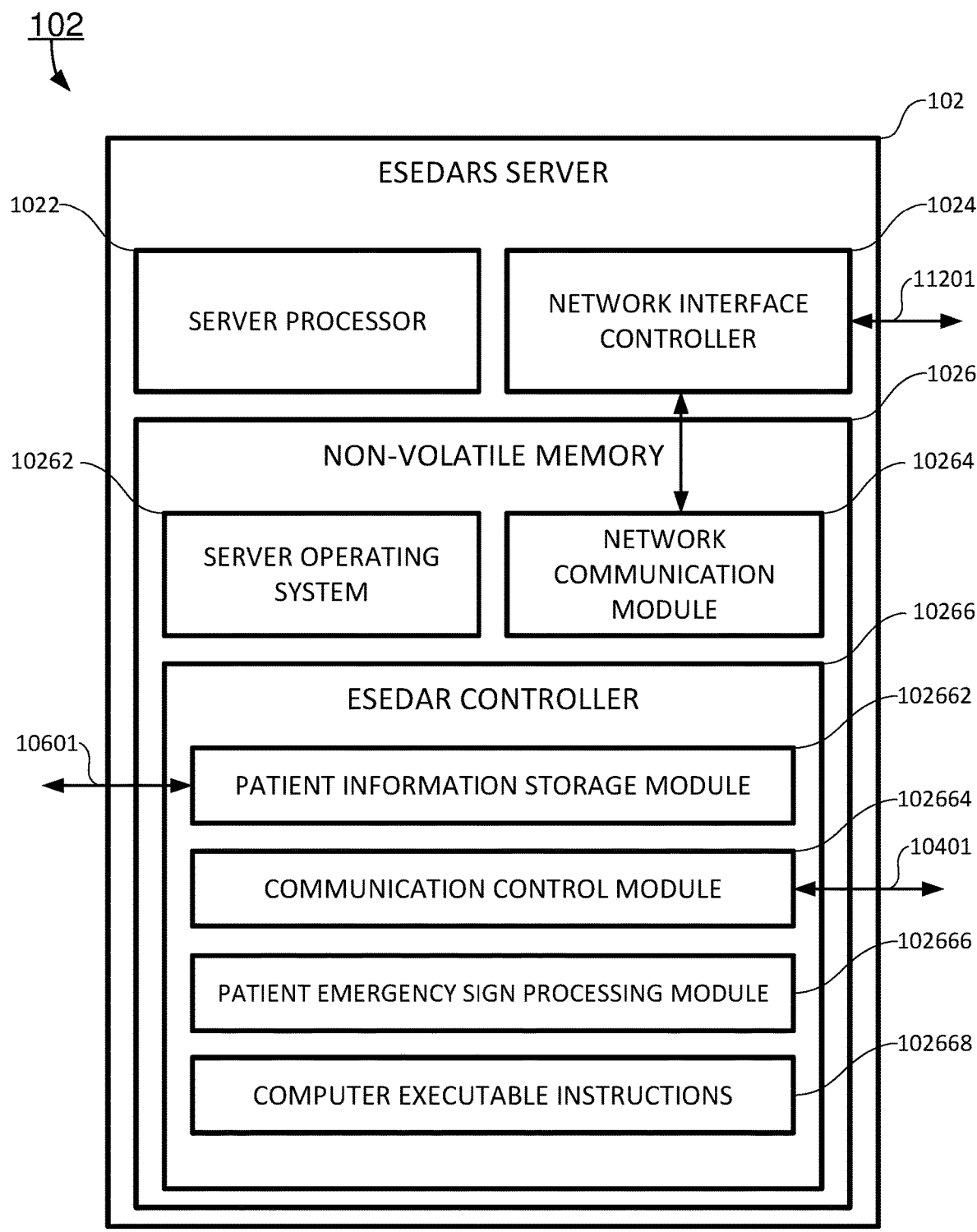
FIG. 2 illustrates a block diagram of an ESEDARS server of the ESEDARS according to certain embodiments of the present disclosure.

In certain embodiments, as shown in FIG. 2, the ESEDARS server 102 includes: a server processor 1022, a network interface controller 1024, and a non-volatile memory 1026. The server processor 1022 controls operations of the ESEDARS 100. The network interface controller 1024 connects to the communication network 110 through a firewall connector 11201 over a firewall 112. The non-volatile memory 1026 stores a server operating system 10262, a network communication module 10264, and an ESEDAR controller 10266. The ESEDAR controller 10266 includes a patient information storage module 102662 for accessing the patient database 106 through a database interface 10601, a communication control module 102664 for facilitating communication to the communication system 104 through a communication control interface, a patient emergency signs processing module 102666, and computer executable instructions 102668. When executed by the server processor 1022, the computer executable instructions 102668 perform one or more of following operations, not necessarily in the following order:

receiving, through patient biological information transmission channels 141 from an ESEDARS personal device 120 of a patient 130, patient biological information constantly monitored and collected by a set of PBICDs 140 of the ESEDARS personal device 120;

processing, by the patient emergency signs processing module 102666, patient biological information received, based on base line patient biological information from the patient database 106;

initiating, by the ESEDARS server 102, an emergency voice call to the ESEDARS personal device 120 of the patient 130 through the communication system 104, when at least one of the set of PBICDs 140 detects certain type of biological information that exceeds a normal range of the set of baseline biological information stored in the patient database 106;

initiating, by the ESEDARS server 102, an emergency call to the nearby emergency dispatch center 108 to notify the live emergency responder 1081 with the patient's GPS location information and patient information including contact information of patient's relatives, friends and other responders on record;

connecting, through the communication control module 102664, the ESEDARS personal device 120 carried by the patient 130 to the patient's relatives, friends and other responders on record and a nearby medical facility to coordinate immediate medical assistance to the patient 130;

transmitting, through the communication control module 102664, a set of patient specific medical assistance instructions through the communication control interface and the live emergency responder 1081 for the patient 130 to follow including instructing the patient to take one or more patient specific emergency medicines stored in the emergency medicine storage 1208 of the ESEDARS personal device 120, and maintaining, communication between the patient 130 and the live emergency responder 1081 and the one or more patient's relatives, friends and other responders on record until an ambulance from the nearby medical facility arrives.

In certain embodiments, the ESEDARS personal device 120 collects patient biological information from the set of PBICDs 140 connected through the patient biological information transmission channels 141. In certain embodiments, the patient biological information includes: speech samples, facial images and video, electroencephalography (EEG) data, electrocardiography (ECG/EKG) data, breath samples, blood glucose content, blood oxygen content, pulse rate, blood pressure, sound samples such as breathing, heart, thoracic, arterial, intravenous, uterine, fetal, intestinal and other sounds, and body temperatures at various time. The baseline biological information stored in the patient database 106 may include: normal speech samples including tempo, pitch, and intensity of speech, normal facial images and normal walking videos of the patient 130 from many different angles and directions, normal electroencephalography (EEG) data, normal electrocardiography (ECG/EKG) data, normal breath samples, normal blood glucose content range, normal blood oxygen content range, normal pulse rate range, normal blood pressure range, normal sound samples such as breathing, heart, thoracic, arterial, intravenous, uterine, fetal, intestinal and other sounds, and normal body temperatures range at various time.

Figure 6:
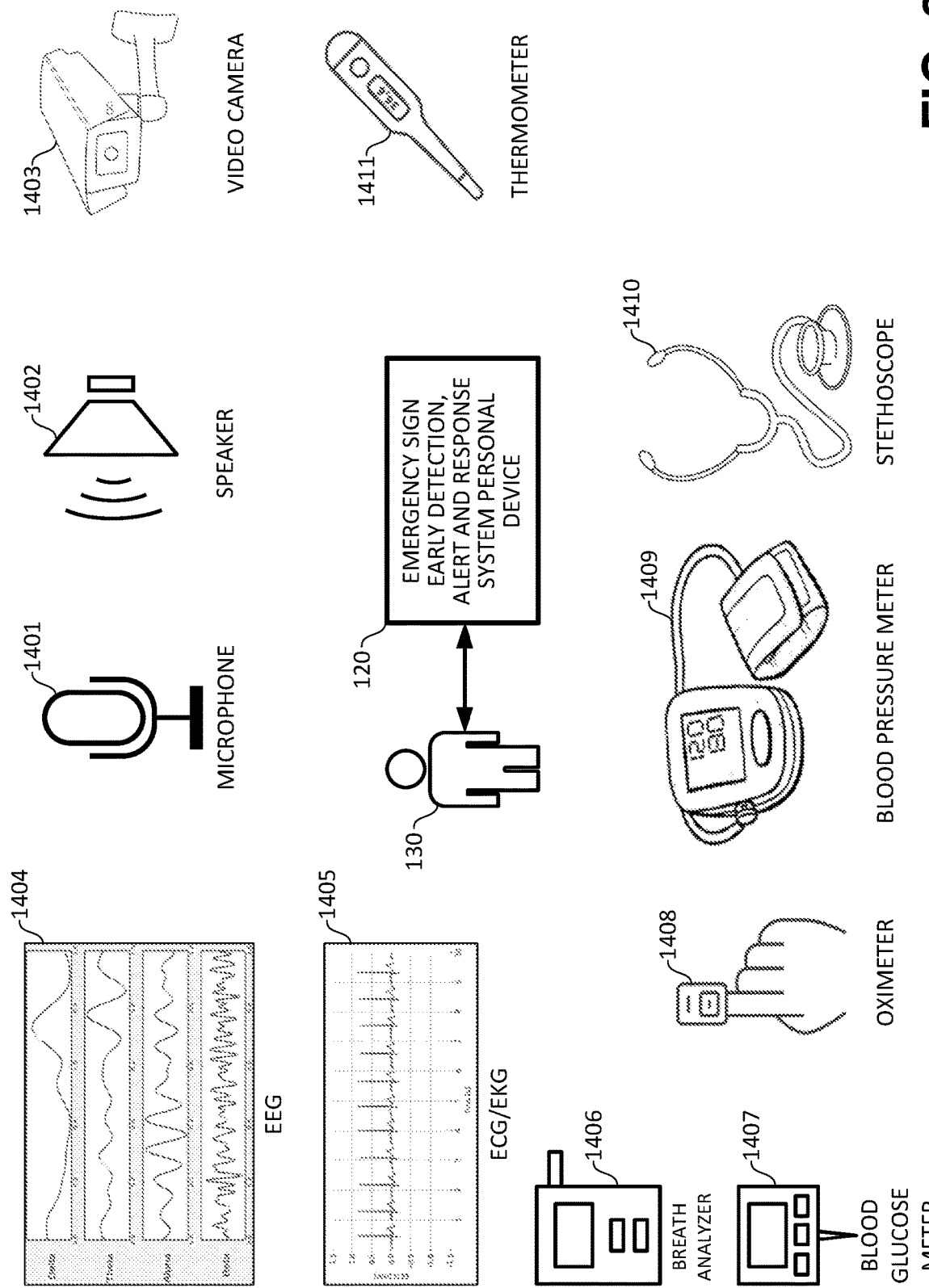
FIG. 6 shows an exemplary set of PBICDs according to certain embodiments of the present disclosure.

In certain embodiments, as shown in FIG. 6, the set of PBICDs 140 includes: a microphone 1401 and a speaker 1402, one or more video cameras 1403, one or more electroencephalograms 1404, one or more electrocardiograms 1405, a breath analyzer 1406, a blood glucose meter 1407, an oximeter 1408, a blood pressure meter 1409, a stethoscope 1410, and a thermometer 1411.

In certain embodiments, as shown in FIGS. 5 and 6, the microphone 1401 and the speaker 1402 are used to allow the patient 130 to make and receive voice calls, to generate voice samples of the patient 130, and to provide voice instructions to the patient 130. The microphone 1401 is used to collect speech samples of the patient 130. When the patient 130 is experiencing difficulty speaking, the speech samples collected will deviate from the normal speech patterns, for example, the tempo of the speech, the pitch, the intensity may change dramatically. These deviations may be picked up through a patient emergency signs processing module 120668 of the ESEDARS personal device 120 and the patient emergency signs processing module 102666 of the ESEDARS server 102 through speech processing using artificial intelligence algorithms. When these speech parameters such as the tempo, the pitch, and the intensity are determined to exceed a normal range of these speech parameters, the ESEDARS server 102 determines that the patient 130 is near or in an emergency condition.

In certain embodiments, the voice data from the user is used as user's identifier the same way as the fingerprinting as the fingerprinting to determine the user's identity. In certain embodiments, as shown in FIG. 5, the video cameras 1403 may be used with a display screen 1205 to receive and display text messages and carry out video calls. Additionally, the video cameras 1403 are also used to monitoring the patient 130 through videos and still images. In one embodiment, a video camera 1403 is equipped on a portable ESEDARS personal device 120, as shown in FIG. 5. In another embodiments, a video camera 1403 is installed on the wall of a room the patient stays in most of times, such as a room in a house, or room in an office, as shown in FIG. 6. The wall-mount camera 1403 may be wirelessly connected to the ESEDARS personal device 120 through the patient biological information transmission channels 141. The video cameras 1403 are used to collect videos and still images of the patient 130 during his/her daily life. The baseline biological information of the patient 130 includes normal facial images and normal walking videos of the patient 130 from many different angles and directions. Pre-stroke patient may experience certain facial expression changes such as facial paralysis, and walking patterns may also change. These deviations may be picked up through a patient emergency signs processing module 120668 of the ESEDARS personal device 120 and the patient emergency signs processing module 102666 of the ESEDARS server 102 through image and video processing using artificial intelligence algorithms. When these facial expressions and walking patterns of the patient 130 are determined to exceed a normal range of baseline images or baseline videos, the ESEDARS server 102 determines that the patient 130 is near or in an emergency condition.

In certain embodiments, as shown in FIG. 6, the electroencephalograms 1404 are used for monitoring electroencephalography of the patient 130. Due to the expensive nature of the electroencephalograms 1404, the patient 130 may not be able to afford to have an electroencephalogram 1404 installed at home or office. However, the ESEDARS personal device 120 may include wireless interfaces to the electroencephalogram 1404 installed in doctor's office, and the patient 130 may be able to go to doctor's office regularly and obtain electroencephalography of the patient 130. The ESEDARS personal device 120 receives electroencephalography data through the patient biological information transmission channels 141 and transmits the electroencephalography data received to the patient emergency signs processing module 102666 of the ESEDARS server 102 through electroencephalographical data processing using artificial intelligence algorithms. When the electroencephalographical data received and analyzed deviates substantially from the normal baseline electroencephalographical data, the ESEDARS server 102 determines that the patient 130 is near or in an emergency condition.

In certain embodiments, as shown in FIG. 6, the electrocardiograms 1405 are used for monitoring electrocardiography of the patient 130. Full featured electrocardiograms 1405 may be found from doctor's offices, however, basic electrocardiograms 1405 may be found in wearable mobile devices such as Apple Watches. The patient 130 can use the full-featured electrocardiograms 1405 occasionally in doctor's office, a smart phone-based electrocardiograms 1405 may be used to monitor electrocardiography data in a continuous manner. The Apple Watch includes sensors to collect and monitor the electrocardiography data of the patient 130, then the electrocardiography data collected is transmitted to an Apple iPhone, and further relayed to the ESEDARS personal device 120 through the patient biological information transmission channels 141. The electrocardiography data collected is transmitted to the patient emergency signs processing module 102666 of the ESEDARS server 102 for electrocardiography data processing using artificial intelligence algorithms. When the electrocardiography data received and analyzed deviates substantially from the normal baseline electrocardiography data, the ESEDARS server 102 determines that the patient 130 is near or in an emergency condition.

In certain embodiments, as shown in FIG. 6, the breath analyzer 1406 is used to analyze breath samples of the patient 130. The breath analyzer 1406 tests many elements such as blood alcohol level, nicotine, hard to digest food components such as lactose, fructose, sorbitol, and inulin to monitor the overall health of the patient 130. The breath analyzer 1406 can be made in a small portable package and electronically connected to the ESEDARS personal device 120 through home network, Wi-Fi, and Bluetooth. The results of analyzed breath samples are transmitted to the patient emergency signs processing module 102666 of the ESEDARS server 102 for breath sample data processing using artificial intelligence algorithms. When the analyzed breath sample data received and analyzed deviates substantially from the normal baseline breath sample data, the ESEDARS server 102 determines that the patient 130 is near or in an emergency condition.

In certain embodiments, as shown in FIG. 6, the blood glucose meter 1407, the oximeter 1408, and the blood pressure meter 1409 are all related to blood and heart beats of the patient 130. The blood glucose meter 1407 monitors the blood sugar of the patient 130. The oximeter 1408 monitors pulse rate and blood oxygen content of the patient 130. The blood pressure meter 1409 monitors pulse rate and blood pressure of the patient 130. The blood glucose meter 1407, the oximeter 1408, and the blood pressure meter 1409 can be made into compact and portable forms, and can be wirelessly connected to the ESEDARS personal device 120. Regular monitoring using the blood glucose meter 1407, the oximeter 1408, and the blood pressure meter 1409 can ensure the heart and blood vessel's health of the patient 130 and detect emergency signs before a stroke or heart attack happens. The blood glucose meter 1407 is very important electronic equipment for diabetic patients.

In certain embodiments, as shown in FIG. 6, the stethoscope 1410 is used for monitoring breathing, heart, murmurs, Atrial Fibrillation (AFib), thoracic, arterial, intravenous, uterine, fetal, intestinal and other sounds of the patient 130. Electronic stethoscope includes sensors to collect and monitor breathing, heart, thoracic, arterial, intravenous, uterine, fetal, intestinal and other sounds of the patient 130, then various sound samples collected are transmitted to the ESEDARS personal device 120 through the patient biological information transmission channels 141. The various sound samples collected are then transmitted to the patient emergency signs processing module 102666 of the ESEDARS server 102 for sound signal processing using artificial intelligence algorithms. When the various sound samples received and analyzed deviate substantially from the normal baseline corresponding sound samples, the ESEDARS server 102 determines that the patient 130 is near or in an emergency condition.

In certain embodiments, as shown in FIG. 6, the thermometer 1411 is used to monitor body temperature of the patient 130. Electronic thermometer 1411 may include various temperature sensors and these temperature sensors may be placed in predetermined locations of the patient 130. These sensors collect and monitor body temperatures of the patient 130 in predetermined intervals. The temperatures collected are transmitted to the ESEDARS personal device 120 through the patient biological information transmission channels 141. The temperatures collected are then transmitted to the patient emergency signs processing module 102666 of the ESEDARS server 102 for temperature processing using artificial intelligence algorithms. When the temperatures received and analyzed deviate substantially from the normal baseline corresponding temperature data, or body temperature of the patient 130 exhibits sudden change, the ESEDARS server 102 determines that the patient 130 is near or in an emergency condition.

Figure 3:
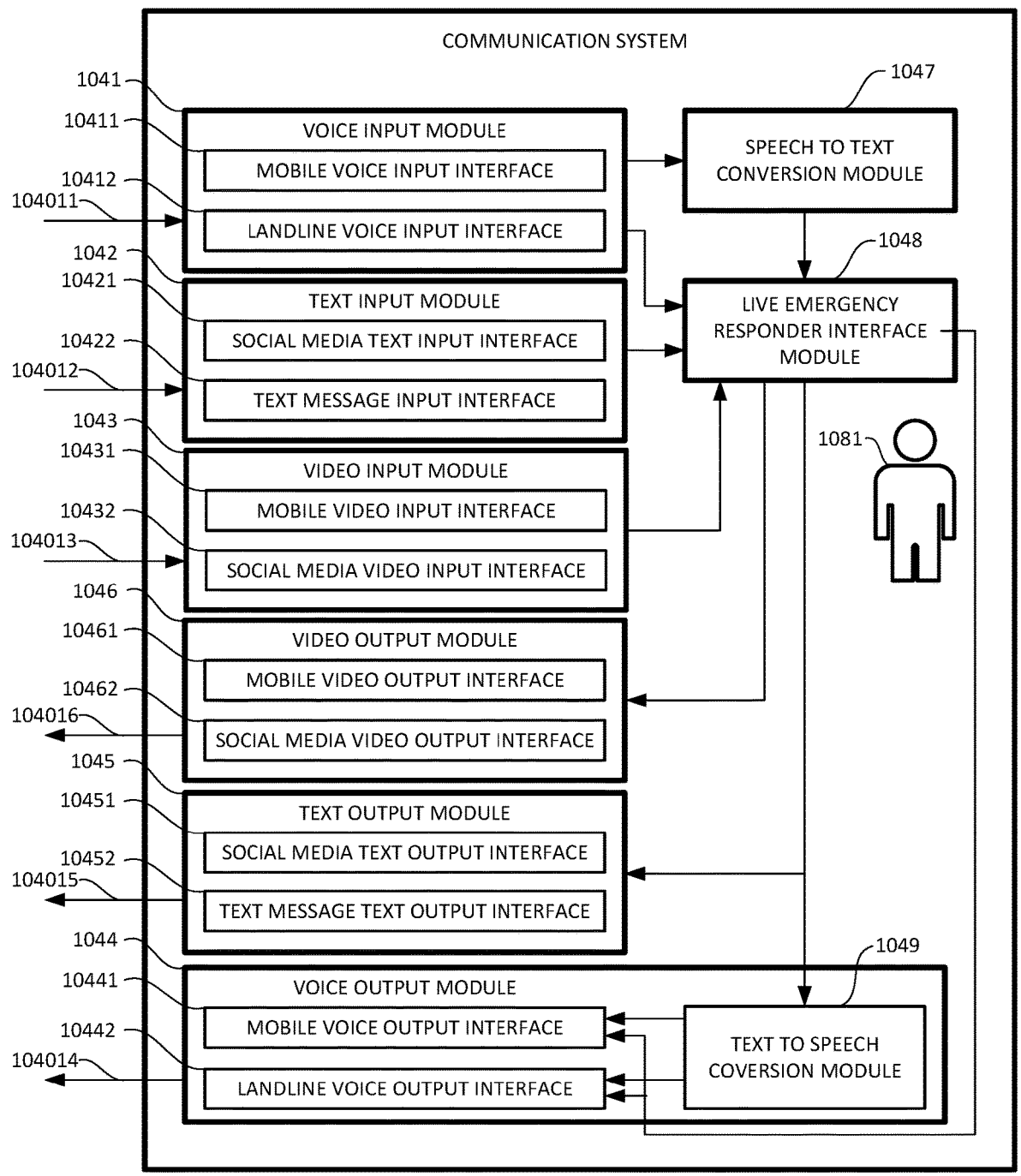
FIG. 3 illustrates a block diagram of a communication system of the ESEDARS according to certain embodiments of the present disclosure.

In certain embodiments, as shown in FIG. 3, the communication system 104 includes: a voice input module 1041, a text input module 1042, a video input module 1043, a voice output module 1044, a text output module 1045, and a video output module 1046.

In certain embodiments, the voice input module 1041 includes a mobile voice input interface 10411 to receive mobile voice calls, and a landline voice input interface 10412 to receive landline voice calls. The text input module 1042 having a social media text input interface 10421 to receive text messages through the social media platforms, and a text message input interface 10422 to receive text messages through mobile phones. The video input module 1043 includes a mobile video input interface 10431 to receive video calls over the mobile phones, and a social media video input interface 10432 to receive video calls through the social media platforms.

In certain embodiments, the voice output module 1044 includes a mobile voice output interface 10441 to make mobile voice calls, and a landline voice output interface 10442 to make landline voice calls. The text output module 1045 includes a social media text output interface 10451 to transmit text messages through the social media platforms, and a text message output interface 10452 to transmit text messages through the mobile phones. The video output module 1046 includes a mobile video output interface 10461 to make video calls over the mobile phones, and a social media video output interface 10462 to make video calls through the social media platforms.

In certain embodiments, the communication system 104 also includes: a speech to text conversion module 1047 for converting voice input to text input, a live emergency responder interface module 1048 for the live emergency responder 1081 to receive and make conference calls among the patient 130, the live emergency responder 1081, the patient's relatives, friends and other responders on record and the nearby medical facility through voice calls, text messages, and video calls, and a text to speech conversion module 1049 to make voice calls to the patient 130 through the ESEDARS personal device 120.

In certain embodiments, the communication system connector 10401 includes: a voice input terminal 104011 connected to the voice input module 1041, a text input terminal 104012 connected to the text input module 1042, a video input terminal 104013 connected to the video input module 1043, a voice output terminal 104014 connected to the voice output module 1044, a text output terminal 104015 connected to the text output module 1045, and a video output terminal 104016 connected to the video output module 1046.

In certain embodiments, the communication among the patient 130, the live emergency responder 1081, the patient's relatives, friends and other responders on record and the nearby medical facility includes: a mobile voice call, a mobile videotelephony call, a landline voice call, a videotelephony call over the Internet, a text message over a mobile phone, a text message over various social media platforms, and a videotelephony call over the social media platforms.

In certain embodiments, as shown in FIG. 4, the ESEDARS personal device 120 includes: a processor 1202, a network interface controller 1204, an emergency medicine storage 1208, and a non-volatile memory 1206. The processor 1202 controls operations of the ESEDARS personal device 120. The network interface controller 1204 facilitates the communication among the ESEDARS personal device 120, the ESEDARS server 102 and the communication system 104. The emergency medicine storage 1208 includes one or more emergency medicine compartments. In one embodiment, the emergency medicine storage 1208 includes a first compartment 12081 and a second compartment 12082. These emergency medicine compartments are used to store the patient specific emergency medicines. Various sizes of emergency medicine storage 1208 of ESEDARS personal devices 120 may be available to accommodate various size emergency medicines for various high risk patients 130 with various known diseases.

In certain embodiments, the non-volatile memory 1206 stores an operating system 12062, a GPS module 12064 for detecting the GPS location of the patient 130 carrying the ESEDARS personal device 120, and a patient emergency signs early detection, alert and response (ESEDAR) controller 12066. The patient ESEDAR controller 12066 includes a patient information storage module 120662 for storing the patients' information, a patient communication control module 120664 for facilitating communication through the network interface controller 1204 to the ESEDARS server 102 and the communication system 104 over the communication network 110, a patient emergency signs processing module 120666 and computer executable instructions 120668. When executed by the processor 1202, the computer executable instructions 120668 perform one or more of following operations, not necessarily in the following order:

receiving, through the patient biological information transmission channels 141 from an ESEDARS personal device 120, patient biological information constantly monitored and collected by the set of PBICDs 140 of the ESEDARS personal device 120;

transmitting, through the patient communication control module 120664, patient biological information received to the ESEDARS server 102 for processing by the patient emergency signs processing module 102666;

receiving, from the ESEDARS server 102, at least voice communication through the communication system 104 directly, when at least one of the set of PBICDs 140 detects certain type of biological information that exceeds a normal range of the set of baseline biological information stored in the patient database 106;

initiating, by the ESEDARS personal device 120, an emergency call to the nearby emergency dispatch center 108 to notify the live emergency responder 1081 with the patient's GPS location information and patient information including contact information of patient's relatives, friends and other responders on record;

connecting, the ESEDARS personal device 120 to the patient's relatives, friends and other responders on record and a nearby medical facility through the patient communication control module 120664 to coordinate immediate medical assistance to the patient 130 based on the patient information from the patient information storage module 120662;

receiving, through the ESEDARS personal device 120, a set of patient specific medical assistance instructions from the live emergency responder 1081 for the patient 130 to follow including instructing the patient to take one or more patient specific emergency medicines stored in the emergency medicine storage 1208 of the ESEDARS personal device 120; and maintaining, communication between the patient 130 and the live emergency responder 1081 and the one or more patient's relatives, friends and other responders on record until an ambulance from the nearby medical facility arrives.

In certain embodiments, as shown in FIG. 5, the ESEDARS personal device 120 includes at least a microphone 12091 and a speaker 12092 for the patient 130 to make and receive voice calls. In certain embodiments, the ESEDARS personal device 120 further includes a display screen 1205. In one embodiment, the patient 130 uses the display screen 1205 to receive and display text messages. In another embodiment, the patient 130 uses the display screen 1205 to carry out video calls.

In certain embodiments, as shown in FIG. 5, the ESEDARS personal device 120 includes a SIM card holder 1207 to hold a SIM card for mobile communication capable ESEDARS personal device 120.

In certain embodiments, the social media platforms include, but not limited to: Facebook, YouTube, Telegram, Parler, WhatsApp, Messenger, WeChat, Instagram, QQ, Tumblr, Qzone, Tik Tok, Sina Weibo, Twitter, Reddit, Baidu Tieba, LinkedIn, Viber, Snappchat, and Pinterest and various combination of these social media platforms.

Figure 7:
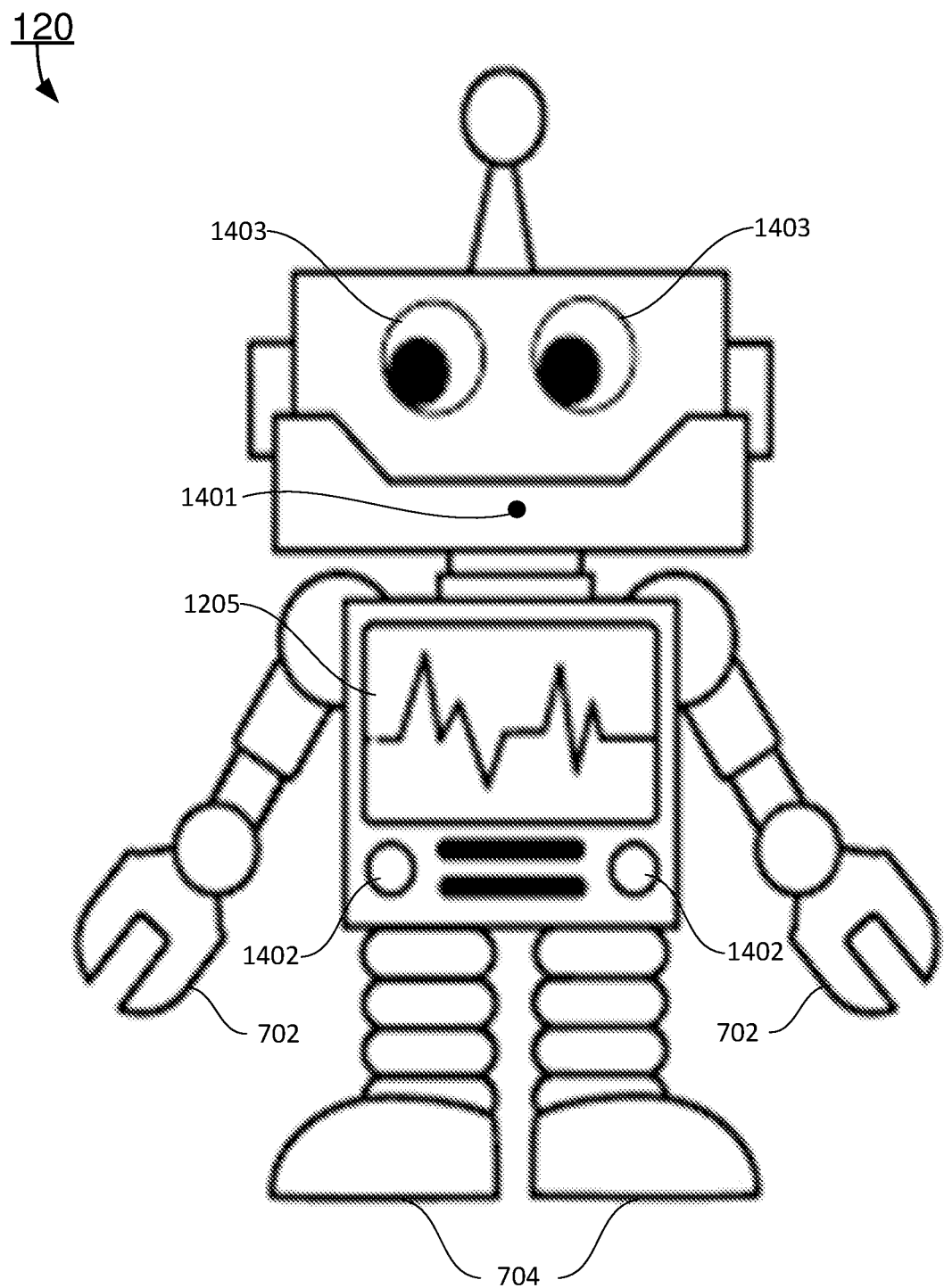
FIG. 7 shows an exemplary robot as an ESEDARS personal device according to certain embodiments of the present disclosure.

In one embodiment, as shown in FIG. 7, the ESEDARS personal device 120 is a robot. The robot 120 has at least one pair of robotic arms 702 to perform certain medical assistance such as carrying out certain medical tests. The robot 120 also has at least one pair of robotic feet 704 to follow the patient 130 around his/her home and/or office, and monitor the patient 130's biological information through the PBICDs. The robot 120 has eyes (video cameras 1403), ears (microphone 1401) and mouth (speakers 1402) to monitor the patient facial expression, walking, and speaking. Following patient behaviors may be considered abnormal, and it is worth further investigation: (1) when the facial expressions become very animated and unsymmetrically, (2) when the patient drags his feet, walking much slower than usual, or having difficulty walking, (3) when the patient having difficulty speaking clearly, talking much slower than usual, having difficulty choosing the words, and having difficulty carrying out normal conversation. Under these circumstances, the robot 120 may offer some assistance to measure the blood pressure, heart beat rate, blood sugar level, blood oxygen level using certain equipment the robot 120 carries such as EEG 1404, ECG/EKG 1405, blood glucose meter 1407, Oximeter 1408, blood pressure meter 1409, stethoscope 1410. After preliminary examinations, and when the robot 120 determines that the patient 130 is in danger of suffering severer medical issues, the robot 120 may contact the ESEDARS for further assistance.

In another embodiment, the ESEDARS personal device is a portable ESEDARS personal device. The portable ESEDARS personal device is carried with the patient and the portable ESEDARS personal device also stores one or more patient specific emergency medicines. In yet another embodiment, the portable ESEDARS personal device is a stationary ESEDARS personal device. The stationary ESEDARS personal device is placed at home or work place of the patient and the stationary ESEDARS personal device also stores one or more patient specific emergency medicines. In yet another embodiment, the ESEDARS personal device can be a group of public stationary ESEDARS personal devices. These public stationary ESEDARS personal devices are placed in public places and each of the public stationary ESEDARS personal devices stores at least one of several common emergency medicines.

In another aspect, the present disclosure relates to a method 800 of using an ESEDARS 100. In certain embodiments, the method 800 includes:

registering, by a group of patients 130, each of the group of patients 130, and a corresponding ESEDARS personal device 120, at an ESEDARS server 102 of the ESEDARS 100, collecting, a set of baseline biological information for each patient 130, and storing the baseline biological information collected in the patient database 106, patient information of each of the patients 130 is stored in a patient database 106 of the ESEDARS 100, and the ESEDARS 100 provide immediate emergency assistance to each of the patients 130 when an ESEDARS personal device 120 detects one or more emergency signs from a corresponding patient 130;

constantly monitoring and collecting, by a set of PBICDs 140 of the group of ESEDARS personal devices 120, patient biological information of each of the patients 130;

receiving, through a patient communication control module 120664 from an ESEDARS personal device 120, the patient biological information constantly monitored and collected by the set of PBICDs 140 of the ESEDARS personal device 120;

processing, through a patient emergency signs processing module 102666 of the ESEDARS server 102 of the ESEDARS 100, the patient biological information received, and comparing the patient biological information received with the set of baseline biological information stored in the patient database 106;

initiating, by the ESEDARS server 102, at least voice communication between the ESEDARS server 102 and the ESEDARS personal device 120 of the patient 130 through the communication system 104 directly, when at least one of the set of PBICDs 140 detects certain type of biological information that exceeds a normal range of the set of baseline biological information stored in the patient database 106;

initiating, by the ESEDARS server 102, an emergency call to a nearby emergency dispatch center 108 to notify a live emergency responder 1081 with the patient's GPS location information and patient information including contact information of patient's relatives, friends and other responders on record;

connecting, by the live emergency responder 1081, to one or more patient's relatives, friends and other responders on record and a nearby medical facility to coordinate immediate medical assistance to the patient 130 based on the patient information received and retrieved from the patient database 106;

providing, by the live emergency responder 1081 and the ESEDARS server 102, patient specific medical assistance instructions for the patient 130 to follow including instructing the patient 130 to take one or more patient specific emergency medicines stored in an emergency medicine storage 1208 of the ESEDARS personal device 120; and communicating, by the patient 130 through a communication system 104 of the ESEDARS 100, with the live emergency responder 1081 and the one or more patient's relatives, friends and other responders on record until an ambulance from a nearby medical facility arrives.

Figure 8:
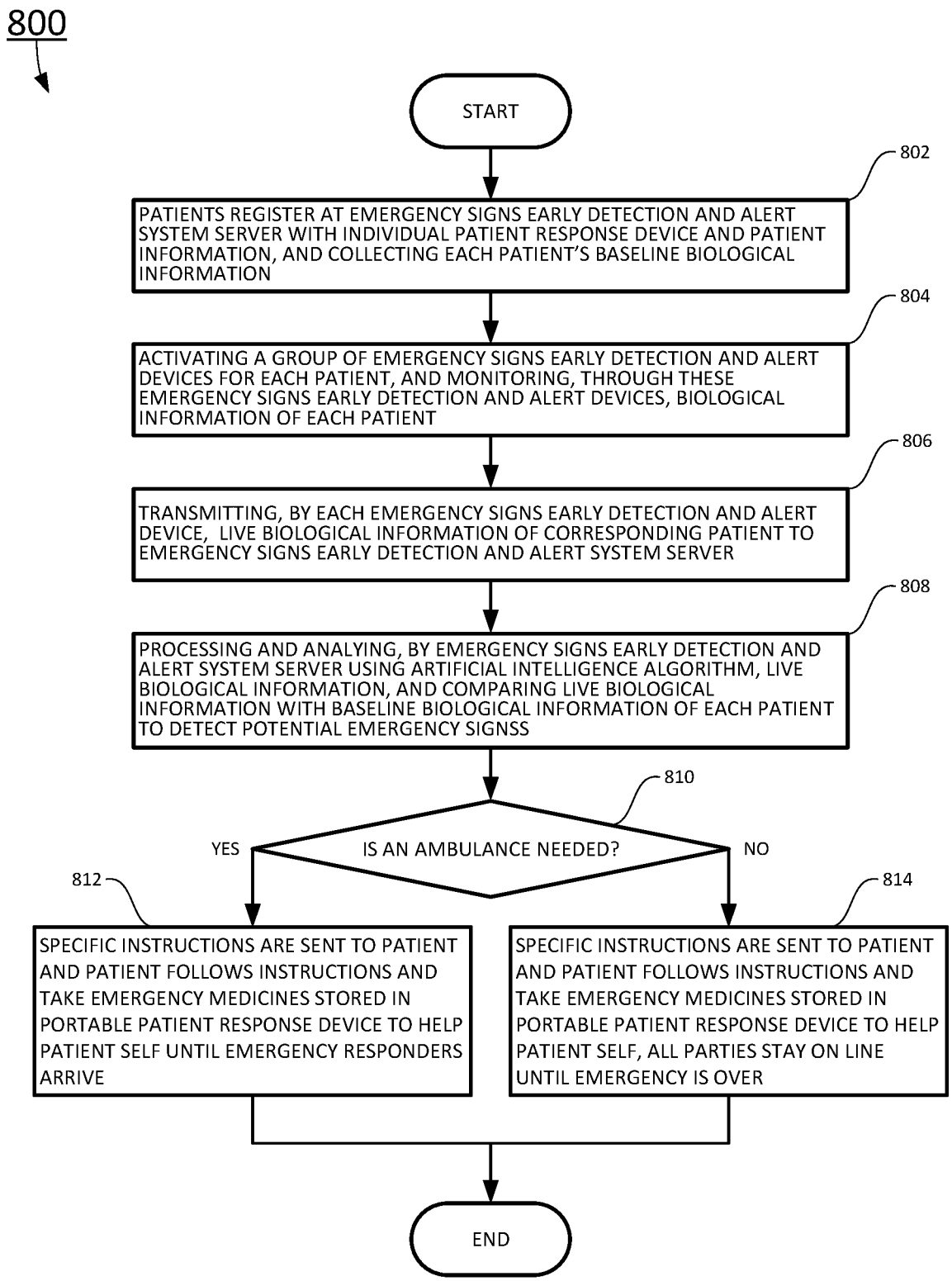
FIG. 8 shows a flow chart of a method of using the ESEDARS according to certain embodiments of the present disclosure.

FIG. 8 shows a flow chart of the method 800 of using the ESEDARS 100 according to certain embodiments of the present disclosure.

At block 802, each of a group of patients 130 registers the patient himself/herself, and one corresponding ESEDARS personal devices 120, at an ESEDARS server 102 of the ESEDARS 100, collecting, a set of baseline biological information for each patient 130, and storing the baseline biological information collected in the patient database 106, patient information of each of the patients 130 is stored in a patient database 106 of the ESEDARS 100, and the ESEDARS 100 provide immediate emergency assistance to each of the patients 130 when an ESEDARS personal device 120 detects one or more emergency signs from a corresponding patient 130. The ESEDARS 100 includes a network of emergency dispatch centers 108 to provide immediate emergency assistance to the patients 130 when emergencies occur to the registered patients 130.

At block 804, each of the ESEDARS personal device 120 is activated at the ESEDARS server 102 of the ESEDARS 100, and each of the ESEDARS personal devices 120 monitors biological information of each patient 130 through a set of PBICDs 140. In certain embodiments, the patient biological information includes: speech samples, facial images and video, electroencephalography (EEG) data, electrocardiography (ECG/EKG) data, breath samples, blood glucose content, blood oxygen content, pulse rate, blood pressure, sound samples such as breathing, heart, thoracic, arterial, intravenous, uterine, fetal, intestinal and other sounds, and body temperatures at various time.

At block 806, the biological information of each patient 130 through the set of PBICDs 140 is collected and transmitted to the ESEDARS server 102 through a communication network 110.

At block 808, the ESEDARS server 102 processes and analyzes the live patient biological information received from each patient 130 using artificial intelligence algorithms and comparing the live patient biological information received from each patient 130 with corresponding patient baseline biological information stored in the patient database, and determines whether an emergency is about to happen to a patient 130.

When at least one of the set of PBICDs 140 detects certain type of biological information that exceeds a normal range of the set of baseline biological information of the patient 130 stored in the patient database 106, the ESEDARS server 102 initiates at least voice communication between the ESEDARS server 102 and the ESEDARS personal device 120 of the patient 130 through the communication system 104 directly to notify the patient 130 that there is high possibility that an medical emergency is about to happen to the patient 130.

The ESEDARS server 102 initiates an emergency call to a nearby emergency dispatch center 108 to notify a live emergency responder 1081 with the patient's GPS location information and patient information including contact information of patient's relatives, friends and other responders on record. The live emergency responder 1081 connects to one or more patient's relatives, friends and other responders on record and a nearby medical facility to coordinate immediate medical assistance to the patient 130 based on the patient information received and retrieved from the patient database 106.

At query block 810, based on the severity of the emergency, patient medical history, and other patient information, the artificial intelligence algorithms of the ESEDARS server 102, the live emergency responder 1081, the patient 130, as well as one or more patient's relatives, friends and other responders on record determines whether an ambulance is needed for this emergency. When the answer is yes, the method 800 proceeds to block 812 to coordinate the arrangement of the ambulance from nearby medical emergency facilities. Otherwise, the method 800 proceeds to block 814 to coordinate the patient 130 to help himself/herself without the ambulance.

At block 812, when the ambulance is needed, the live emergency responder 1081 notifies the nearby emergency medical facility to send the ambulance and patient specific professional staffs to assist the patient 130. In the meantime, patient specific medical assistance instructions for the patient 130 to follow are sent to the patient 130. These patient specific medical assistance instructions include necessary steps the patient 130 can perform and instructions to take one or more patient specific emergency medicines stored in the emergency medicine storage 1208 of the ESEDARS personal device 120, until the ambulance and the patient specific professional staffs arrive.

At block 814, when the ambulance is not needed, patient specific medical assistance instructions for the patient 130 to follow are sent to the patient 130. These patient specific medical assistance instructions include necessary steps the patient 130 can perform and instructions to take one or more patient specific emergency medicines stored in the emergency medicine storage 1208 of the ESEDARS personal device 120. The patient 130 stays online with the live emergency responder 1081, the patient's relatives, friends and other responders on record, and emergency medical staff until the emergency is over.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed is:

1. An emergency signs early detection, alert and response system, comprising:

an emergency signs early detection, alert and response system (ESEDARS) server, wherein each of a plurality of patients and a corresponding ESEDARS personal device each patient carries are registered at the ESEDARS server, a set of baseline biological information for each patient is collected and stored in a patient database, and the ESEDARS server provides immediate emergency assistance to a patient when an ESEDARS personal device of the patient detects one or more emergency signs from the patient;

the patient database connected to and accessible by the ESEDARS server, wherein the patient database stores patient information of the plurality of patients, wherein the patient information comprises personal information, medical history, a set of baseline biological information, patient contact information, and contact information of relatives, friends and other responders and local medical facilities to be notified;

a communication system connected to the ESEDARS server, wherein the communication system provides voice, text, and video communication over a communication network among the patient, one or more live emergency responders from a nearby emergency dispatch center, one or more patient's relatives, friends and other responders on record, and one or more nearby medical facilities to provide immediate emergency assistance to the patient when emergency occurs; and a plurality of ESEDARS personal devices, wherein each patient carries a corresponding ESEDARS personal device, and each ESEDARS personal device is in communication with a plurality of patient biological information collection devices (PBICD), wherein the plurality of PBICDs constantly monitors the biological information of the patient and transmits the patient biological information collected to the ESEDARS server through the ESEDARS personal device, and when at least one of the plurality of PBICDs detects certain type of biological information that exceeds a normal range of the set of baseline biological information stored in the patient database, the ESEDARS personal device initiates at least voice communication between the ESEDARS server and the ESEDARS personal device of the patient through the communication system autonomously, and an emergency medicine storage for storing one or more patient specific emergency medicines to be used when emergency occurs, wherein an ESEDARS personal device indicator of the ESEDARS personal device is lit in green light indicating the ESEDARS personal device is in normal operation state, when an emergency signs is detected from the patient, the ESEDARS personal device indicator turns red indicating the patient is in an emergency, the ESEDARS personal device initiates at least voice communication between the ESEDARS server and the ESEDARS personal device of the patient through the communication system autonomously and the ESEDARS server initiates an emergency call to the nearby emergency dispatch center to notify a live emergency responder with the patient's GPS location information and patient information including contact information of patient's relatives, friends and other responders on record, the live emergency responder connects to one or more patient's relatives, friends and other responders on record and a nearby medical facility to coordinate immediate medical assistance to the patient based on the patient information received and retrieved from the patient database, and the live emergency responder and the ESEDARS server provide patient specific medical assistance instructions for the patient to follow including instructing the patient to take one or more patient specific emergency medicines stored in the emergency medicine storage of the ESEDARS personal device, and the patient continues to communicate with the live emergency responder and the one or more patient's relatives, friends and other responders on record until an ambulance from a nearby medical facility arrives.

2. The emergency signs early detection, alert and response system according to claim 1, wherein the communication network comprises a wireless personal area network (WPAN) having a Wi-Fi network, a Bluetooth network, an infrared network, and a Zigbee network, a wireless local area network (WLAN), a wireless metropolitan area network (WMAN), a wireless wide area network (WWAN), a cellular network, and a mobile communication network.

3. The emergency signs early detection, alert and response system according to claim 1, wherein the ESEDARS server comprises:
  a server processor for controlling operations of the ESEDARS;
  a network interface controller connected to the communication network through a firewall connector over a firewall; and
  a non-volatile memory for storing an server operating system, a network communication module, and an emergency signs early detection, alert and response (ESEDAR) controller having a patient information storage module for accessing the patient database through a database interface, a communication control module for facilitating communication to the communication system through a communication control interface, a patient emergency signs processing module, and computer executable instructions, when executed by the server processor, the computer executable instructions perform one or more of following operations:
  receiving, through patient biological information transmission channels from an ESEDARS personal devices of a patient, patient biological information constantly monitored and collected by a plurality of PBICDs of the ESEDARS personal devices;
  processing, by the patient emergency signs processing module, patient biological information received, based on base line patient biological information from the patient database;
  receiving, from the ESEDARS personal device, an emergency voice call to the ESEDARS personal device of the patient through the communication system, when at least one of the plurality of PBICDs detects certain type of biological information that exceeds a normal range of the set of baseline biological information stored in the patient database;
  initiating, by the ESEDARS server, an emergency call to the nearby emergency dispatch center to notify the live emergency responder with the patient's GPS location information and patient information including contact information of patient's relatives, friends and other responders on record;
  connecting, through the communication control module, the ESEDARS personal device carried by the patient to the patient's relatives, friends and other responders on record and a nearby medical facility to coordinate immediate medical assistance to the patient; and
  transmitting, through the communication control module, a set of patient specific medical assistance instructions through the communication control interface and the live emergency responder for the patient to follow including instructing the patient to take one or more patient specific emergency medicines stored in the emergency medicine storage of the ESEDARS personal device, and the patient continues to communicate with the live emergency responder and the one or more patient's relatives, friends and other responders on record until an ambulance from the nearby medical facility arrives.

4. The emergency signs early detection, alert and response system according to claim 1, wherein the ESEDARS personal device collects patient biological information from the plurality of PBICDs connected through the patient biological information transmission channels, and the plurality of PBICDs comprises:
  a microphone and a speaker, wherein the microphone and the speaker allow the patient to make and receive voice calls, to generate voice samples of the patient, and to provide voice instructions to the patient;
  one or more video cameras, wherein the video cameras monitor the patient through videos and still images;
  one or more electroencephalograms, wherein the electroencephalograms monitor electroencephalography of the patient;
  one or more electrocardiograms, wherein the electrocardiograms monitor electrocardiography of the patient;
  a breath analyzer, wherein the breath analyzer analyses breath samples of the patient;
  a blood glucose meter, wherein the blood glucose meter monitors blood sugar of the patient;
  an oximeter, wherein the oximeter monitors pulse rate and blood oxygen content of the patient;
  a blood pressure meter, wherein the blood pressure meter monitors pulse rate and blood pressure of the patient;
  a stethoscope, wherein the stethoscope monitors breathing, heart, thoracic, arterial, intravenous, uterine, fetal, intestinal and other sounds of the patient; and
  a thermometer, wherein the thermometer monitors the body temperature of the patient.

5. The emergency signs early detection, alert and response system according to claim 4, wherein the ESEDARS personal device further comprises a display screen to receive and display text messages and carry out video calls.

6. The emergency signs early detection, alert and response system according to claim 5, wherein the communication among the patient, the live emergency responder, the patient's relatives, friends and other responders on record and the nearby medical facility comprises:
  a mobile voice call;
  a mobile videotelephony call;
  a landline voice call;
  a videotelephony call over the Internet;
  a text message over a mobile phone;
  a text message over a plurality of social media platforms; and a videotelephony call over the plurality of social media platforms.

7. The emergency signs early detection, alert and response system according to claim 6, wherein the communication system comprises:
 a voice input module having a mobile voice input interface to receive mobile voice calls, and a landline voice input interface to receive landline voice calls;
 a text input module having a social media text input interface to receive text messages through the plurality of social media platforms, and a text message input interface to receive text messages through mobile phones;
 a video input module having a mobile video input interface to receive video calls over the mobile phones, and a social media video input interface to receive video calls through the plurality of social media platforms;
 a voice output module having a mobile voice output interface to make mobile voice calls, and a landline voice output interface to make landline voice calls;
 a text output module having a social media text output interface to transmit text messages through the plurality of social media platforms, and a text message output interface to transmit text messages through the mobile phones;
 a video output module having a mobile video output interface to make video calls over the mobile phones, and a social media video output interface to make video calls through the plurality of social media platforms;
 a speech to text conversion module for converting voice input to text input;
 a live emergency responder interface module for the live emergency responder to receive and make conference calls among the patient, the live emergency responder, the patient's relatives, friends and other responders on record and the nearby medical facility through voice calls, text messages, and video calls; and
 a text to speech conversion module to make voice calls to the patient through the ESEDARS personal device.

8. The emergency signs early detection, alert and response system according to claim 7, wherein the communication control interface comprises:
 a voice input terminal connected to the voice input module;
 a text input terminal connected to the text input module;
 a video input terminal connected to the video input module;
 a voice output terminal connected to the voice output module;
 a text output terminal connected to the text output module; and
 a video output terminal connected to the video output module.

9. The emergency signs early detection, alert and response system according to claim 1, wherein the ESEDARS personal device comprises:
 a processor, wherein the processor controls operations of the ESEDARS personal device;
 a network interface controller, wherein the network interface controller facilitates the communication among the ESEDARS personal device, the ESEDARS server and the communication system;
 the emergency medicine storage, wherein the emergency medicine storage comprises one or more emergency medicine compartments, where one or more patient specific emergency medicines for the patient are stored; and
 a non-volatile memory, wherein the non-volatile memory stores an operating system, a GPS module for detecting the GPS location of the patient carrying the ESEDARS personal device, and a patient emergency signs early detection, alert and response (ESEDAR) controller having a patient information storage module for storing the patient's information, a patient communication control module for facilitating communication through the network interface controller to the ESEDARS server and the communication system over the communication network, a patient emergency signs processing module and computer executable instructions, when executed by the processor, the computer executable instructions perform one or more of following operations:
 receiving, through the patient biological information transmission channels from the ESEDARS personal devices, patient biological information constantly monitored and collected by the plurality of PBICDs of the ESEDARS personal devices;
 transmitting, through the patient communication control module, patient biological information received to the ESEDARS server for processing by the patient emergency signs processing module;
 initiating at least voice communication between the ESEDARS server and the ESEDARS personal device of the patient through the communication system autonomously, when at least one of the plurality of PBICDs detects certain type of biological information that exceeds a normal range of the set of baseline biological information stored in the patient database;
 initiating, by the ESEDARS server, an emergency call to the nearby emergency dispatch center to notify the live emergency responder with the patient's GPS location information and patient information including contact information of patient's relatives, friends and other responders on record;
 connecting, the ESEDARS personal device to the patient's relatives, friends and other responders on record and a nearby medical facility through the patient communication control module to coordinate immediate medical assistance to the patient based on the patient information from the patient information storage module;
 receiving, through the ESEDARS personal device, the set of patient specific medical assistance instructions from the live emergency responder for the patient to follow including instructing the patient to take one or more patient specific emergency medicines stored in the emergency medicine storage of the ESEDARS personal device; and
 maintaining, communication between the patient and the live emergency responder and the one or more patient's relatives, friends and other responders on record until an ambulance from the nearby medical facility arrives.

10. The emergency signs early detection, alert and response system according to claim 1, wherein the ESEDARS personal device comprises:
 a robot, wherein the robot follows the patient around home and office, monitors the patient's biological information through the PBICDs, when certain irregularities occur, the robot offers more tests and examinations, and provides immediate assistance;
 a portable ESEDARS personal device to be carried with the patient wherein the portable ESEDARS personal device stores one or more patient specific emergency medicines;

a stationary ESEDARS personal device to be placed at home or work place of the patient wherein the stationary ESEDARS personal device stores one or more patient specific emergency medicines; and a plurality of public stationary ESEDARS personal devices to be placed in public places wherein each of the plurality of public stationary ESEDARS personal devices stores at least one of a plurality of common emergency medicines.

11. A method of using an emergency signs early detection, alert and response system, comprising:

registering, by a plurality of patients, each of the plurality of patients, and a plurality of emergency signs early detection, alert and response system (ESEDARS) personal devices, one corresponding ESEDARS personal device for each patient, at an ESEDARS server of the ESEDARS, collecting, a set of baseline biological information for each patient, and storing the baseline biological information collected in a patient database, wherein patient information of each of the plurality of patients is stored in the patient database of the ESEDARS, and the ESEDARS provide immediate emergency assistance to a patient when an ESEDARS personal device of the patient detects one or more emergency signs from the patient;

constantly monitoring and collecting, by a plurality of patient biological information collection devices (PBICD) in communication with the plurality of the ESEDARS personal devices, patient biological information of each of the plurality of patients;

receiving, through a patient communication control module from an ESEDARS personal device, the patient biological information constantly monitored and collected by the plurality of PBICDs of the ESEDARS personal device;

processing, through a patient emergency signs processing module of the ESEDARS server of the ESEDARS, the patient biological information received, and comparing the patient biological information received with a set of baseline biological information stored in the patient database;

initiating, by the ESEDARS personal device, at least voice communication between the ESEDARS server and the ESEDARS personal device of the patient through the communication system autonomously, when at least one of the plurality of PBICDs detects certain type of biological information that exceeds a normal range of the set of baseline biological information stored in the patient database;

initiating, by the ESEDARS server, an emergency call to a nearby emergency dispatch center to notify a live emergency responder with the patient's GPS location information and patient information including contact information of patient's relatives, friends and other responders on record;

connecting, by the live emergency responder, to one or more patient's relatives, friends and other responders on record and a nearby medical facility to coordinate immediate medical assistance to the patient based on the patient information received and retrieved from the patient database;

providing, by the live emergency responder and the ESEDARS server, patient specific medical assistance instructions for the patient to follow including instructing the patient to take one or more patient specific emergency medicines stored in an emergency medicine storage of the ESEDARS personal device; and communicating, by the patient through a communication system of the ESEDARS, with the live emergency responder and the one or more patient's relatives, friends and other responders on record until an ambulance from a nearby medical facility arrives.

12. The method of claim 11, wherein the ESEDARS comprises:

the ESEDARS server, wherein each of the plurality of patients and a corresponding ESEDARS personal device each patient carries are registered at the ESEDARS server, a set of baseline biological information for each of the plurality patients is collected and stored in the patient database, and the ESEDARS server provides immediate emergency assistance to each of the plurality of patients when emergencies occur;

the patient database connected to and accessible by the ESEDARS server, wherein the patient database stores patient information of the plurality of patients, wherein the patient information comprises personal information, medical history, patient contact information, and contact information of relatives, friends and other responders on record and local medical facilities to be notified of each of the plurality of the patients;

the communication system connected to the ESEDARS server, wherein the communication system provides voice, text, and video communication over a communication network among the patient, one or more live emergency responders from the nearby emergency dispatch center, one or more patient's relatives, friends and other responders on record, and one or more nearby medical facilities to provide immediate emergency assistance to the patient when emergency occurs; and the plurality of ESEDARS personal devices, wherein each of the plurality of patients carries one corresponding ESEDARS personal device, and each of the plurality of ESEDARS personal devices comprises the plurality of PBICDs connected through patient biological information transmission channels to monitor each of the plurality of patients and to collect patient biological information of each of the plurality of patients, when at least one of the plurality of PBICDs detects certain type of biological information that exceeds a normal range of the set of baseline biological information stored in the patient database, the ESEDARS personal device initiates at least voice communication between the ESEDARS server and the ESEDARS personal device of the patient through the communication system autonomously.

13. The method of claim 12, wherein the communication network comprises a wireless personal area network (WPAN) having a Wi-Fi network, a Bluetooth network, an infrared network, and a Zigbee network, a wireless local area network (WLAN), a wireless metropolitan area network (WMAN), a wireless wide area network (WWAN), a cellular network, and a mobile communication network.

14. The method of claim 13, the ESEDARS server comprises:

a server processor for controlling operations of the ESEDARS;

a network interface controller connected to the communication network through a firewall connector over a firewall; and a non-volatile memory for storing an server operating system, a network communication module, and an emergency signs early detection, alert and response (ESEDAR) controller having a patient information storage module for accessing the patient database through a database interface, a communication control module for facilitating communication to the communication system through a communication control interface, the patient emergency signs processing module for processing patient biological information, and computer executable instructions, when executed by the server processor, the computer executable instructions perform one or more of following operations:

receiving, through the patient communication control module from the plurality of the ESEDARS personal devices, patient biological information constantly monitored and collected by the plurality of PBICDs of the plurality of ESEDARS personal devices;

processing, through the patient emergency signs processing module, the patient biological information received, and comparing the patient biological information received with the set of baseline biological information stored in the patient database;

initiating, by the ESEDARS personal device, at least voice communication between the ESEDARS server and the ESEDARS personal device of the patient through the communication system autonomously, when at least one of the plurality of PBICDs detects certain type of biological information that exceeds a normal range of the set of baseline biological information stored in the patient database;

initiating, by the ESEDARS server, an emergency call to the nearby emergency dispatch center to notify the live emergency responder with the patient's GPS location information and patient information including contact information of patient's relatives, friends and other responders on record;

connecting, the ESEDARS personal device to the patient's relatives, friends and other responders on record and a nearby medical facility through the patient communication control module to coordinate immediate medical assistance to the patient based on the patient information from the patient information storage module;

transmitting, through the communication control module, a set of patient specific medical assistance instructions through the communication control interface and the live emergency responder for the patient to follow including instructing the patient to take one or more patient specific emergency medicines stored in the emergency medicine storage of the ESEDARS personal device; and maintaining, by the patient, communication with the live emergency responder and the one or more patient's relatives, friends and other responders on record until an ambulance from the nearby medical facility arrives.

15. The method of claim 14, wherein the ESEDARS personal device collects patient biological information from the plurality of PBICDs connected through the patient biological information transmission channels, and the plurality of PBICDs comprises:

a microphone and a speaker, wherein the microphone and the speaker allow the patient to make and receive voice calls, to generate voice samples of the patient, and to provide voice instructions to the patient;

one or more video cameras, wherein the video cameras monitor the patient through videos and still images;

one or more electroencephalograms, wherein the electroencephalograms monitor electroencephalography of the patient;

one or more electrocardiograms, wherein the electrocardiograms monitor electrocardiography of the patient;

a breath analyzer, wherein the breath analyzer analyses breath samples of the patient;

a blood glucose meter, wherein the blood glucose meter monitors blood sugar of the patient;

an oximeter, wherein the oximeter monitors pulse rate and blood oxygen content of the patient;

a blood pressure meter, wherein the blood pressure meter monitors pulse rate and blood pressure of the patient;

a stethoscope, wherein the stethoscope monitors breathing, heart, thoracic, arterial, intravenous, uterine, fetal, intestinal and other sounds of the patient; and a thermometer, wherein the thermometer monitors the body temperature of the patient.

16. The method of claim 15, wherein the ESEDARS personal device further comprises a display screen to receive and display text messages and carry out video calls.

17. The method of claim 16, wherein the communication system comprises:

a voice input module having a mobile voice input interface to receive mobile voice calls, and a landline voice input interface to receive landline voice calls;

a text input module having a social media text input interface to receive text messages through the plurality of social media platforms, and a text message input interface to receive text messages through mobile phones;

a video input module having a mobile video input interface to receive video calls over the mobile phones, and a social media video input interface to receive video calls through the plurality of social media platforms;

a voice output module having a mobile voice output interface to make mobile voice calls, and a landline voice output interface to make landline voice calls;

a text output module having a social media text output interface to transmit text messages through the plurality of social media platforms, and a text message output interface to transmit text messages through the mobile phones;

a video output module having a mobile video output interface to make video calls over the mobile phones, and a social media video output interface to make video calls through the plurality of social media platforms;

a speech to text conversion module for converting voice input to text input;

a live emergency responder interface module for the live emergency responder to receive and make conference calls among the patient, the live emergency responder, the patient's relatives, friends and other responders on record and the nearby medical facility through voice calls, text messages, and video calls; and a text to speech conversion module to make voice calls to the patient through the ESEDARS personal device.

18. The method of claim 17, wherein the communication among the patient, the live emergency responder, the patient's relatives, friends and other responders on record and the nearby medical facility comprises:

a mobile voice call;
a mobile videotelephony call;
a landline voice call;
a videotelephony call over the Internet;
a text message over a mobile phone;
a text message over a plurality of social media platforms; and
a videotelephony call over the plurality of social media platforms; and wherein the communication control interface comprises:

a voice input terminal connected to the voice input module;
a text input terminal connected to the text input module;
a video input terminal connected to the video input module;
a voice output terminal connected to the voice output module;
a text output terminal connected to the text output module; and
a video output terminal connected to the video output module.

19. The method of claim 18, wherein the ESEDARS personal device comprises:
a processor, wherein the processor controls operations of the ESEDARS personal device;
a network interface controller, wherein the network interface controller facilitates the communication among the ESEDARS personal device, the ESEDARS server and the communication system;
the emergency medicine storage, wherein the emergency medicine storage comprises one or more emergency medicine compartments, where one or more patient specific emergency medicines for the patient are stored; and
a non-volatile memory, wherein the non-volatile memory stores an operating system, a GPS module for detecting the GPS location of the patient carrying the ESEDARS personal device, and a patient emergency signs early detection, alert and response (ESEDAR) controller having a patient information storage module for storing the patient's information, the patient communication control module for facilitating communication through the network interface controller to the ESEDARS server and the communication system over the communication network, a patient emergency signs processing module and computer executable instructions, when executed by the processor, the computer executable instructions perform one or more of following operations:
receiving, through the patient biological information transmission channels from the ESEDARS personal devices, patient biological information constantly monitored and collected by the plurality of PBICDs of the ESEDARS personal devices;
transmitting, through the patient communication control module, patient biological information received to the ESEDARS server for processing by the patient emergency signs processing module;
initiating at least voice communication between the ESEDARS server and the ESEDARS personal device of the patient through the communication system autonomously, when at least one of the plurality of PBICDs detects certain type of biological information that exceeds a normal range of the set of baseline biological information stored in the patient database;
initiating, by the ESEDARS personal devices, an emergency call to the nearby emergency dispatch center to notify the live emergency responder with the patient's GPS location information and patient information including contact information of patient's relatives, friends and other responders on record;
connecting, the ESEDARS personal device to the patient's relatives, friends and other responders on record and a nearby medical facility through the patient communication control module to coordinate immediate medical assistance to the patient based on the patient information from the patient information storage module;
receiving, through the ESEDARS personal device, the set of patient specific medical assistance instructions from the live emergency responder for the patient to follow including instructing the patient to take one or more patient specific emergency medicines stored in the emergency medicine storage of the ESEDARS personal device; and
maintaining, communication between the patient and the live emergency responder and the one or more patient's relatives, friends and other responders on record until an ambulance from the nearby medical facility arrives.

20. The method of claim 19, wherein the ESEDARS personal device comprises:
a robot, wherein the robot follows the patient around home and office, monitors the patient's biological information through the PBICDs, when certain irregularities occur, the robot offers more tests and examinations, and provides immediate assistance;
a portable ESEDARS personal device to be carried with the patient wherein the portable ESEDARS personal device stores one or more patient specific emergency medicines;
a stationary ESEDARS personal device to be placed at home or work place of the patient wherein the stationary ESEDARS personal device stores one or more patient specific emergency medicines; and
a plurality of public stationary ESEDARS personal devices to be placed in public places wherein each of the plurality of public stationary ESEDARS personal devices stores at least one of a plurality of common emergency medicines.

* * * * *